(12) United States Patent
Corsa et al.

(10) Patent No.: US 9,290,785 B2
(45) Date of Patent: Mar. 22, 2016

(54) METHOD FOR OBTAINING RECOMBINANT HOST BACTERIAL CELLS THAT PRODUCE HYALURONIC ACID

(75) Inventors: Vincenza Corsa, Abano Terme (IT); Alessandro Negro, Padova (IT); Susanna Vaccaro, Abano Terme (IT); Luciano Messina, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 40 days.

(21) Appl. No.: 13/821,947

(22) PCT Filed: Sep. 9, 2011

(86) PCT No.: PCT/EP2011/065642
§ 371 (c)(1),
(2), (4) Date: Apr. 9, 2013

(87) PCT Pub. No.: WO2012/032154
PCT Pub. Date: Mar. 15, 2012

(65) Prior Publication Data
US 2013/0189740 A1 Jul. 25, 2013

(30) Foreign Application Priority Data
Sep. 9, 2010 (IT) .................. MI10A1642

(51) Int. Cl.
| | |
|---|---|
| C12N 15/63 | (2006.01) |
| C12N 15/75 | (2006.01) |
| C12P 19/26 | (2006.01) |
| C08B 37/08 | (2006.01) |
| C12N 9/04 | (2006.01) |
| C12N 9/10 | (2006.01) |
| C12N 9/12 | (2006.01) |
| C12N 9/92 | (2006.01) |

(52) U.S. Cl.
CPC ............. *C12P 19/26* (2013.01); *C08B 37/0072* (2013.01); *C12N 9/0006* (2013.01); *C12N 9/1051* (2013.01); *C12N 9/1241* (2013.01); *C12N 9/92* (2013.01); *C12N 15/635* (2013.01); *C12N 15/75* (2013.01); *C12Y 101/01022* (2013.01); *C12Y 204/01212* (2013.01); *C12Y 207/07009* (2013.01); *C12Y 503/01009* (2013.01)

(58) Field of Classification Search
None
See application file for complete search history.

(56) References Cited

U.S. PATENT DOCUMENTS

2003/0175902 A1 9/2003 Sloma et al.

FOREIGN PATENT DOCUMENTS

WO WO-99/05297 A1 2/1999

OTHER PUBLICATIONS

Jongsareejit et al., ScienceAsia 33:389-395, 2007.*
Oudega et al., Gen Bank accession No. Z93936, Apr. 18, 2005.*
Zhang et al., Applied and Environmental Microbiology 71(7):4101-4103, Jul. 2005.*
Phan, T. T. P. et al., "Novel plasmid-based expression vectors for intra- and extracellular production of recombinant proteins in *Bacillus subtilis*," Protein Expression and Purification, Academic Press, San Diego, CA, US, Apr. 1, 2006, vol. 46, No. 2, pp. 189-195.
Yu, H. et al., "Metabolic engineering of *Escherichia coli* for biosynthesis of hyaluronic acid," Metabolic Engineering, Academic Press, US, Dec. 24, 2007, vol. 10. No. 1, pp. 24-32.
Widner, B. et al., "Hyaluronic acid production in *Bacillus subtilis*." Applied and Environmental Microbiology, American Society for Microbiology, US, Jul. 1, 2005, vol. 71, No. 1, pp. 3747-3752.
Mao, Z. et al., "A recombinant *E. coli* bioprocess for hyaluronan synthesis," Applied Microbiology and Biotechnology, Springer, Berlin, DE, Mar. 24, 2009, vol. 84, No. 1, pp. 63-69.
Chien, L. et al., "Enhanced hyaluronic acid production in *Bacillus subtillis* by coexpressing bacterial hemoglobin," Biotechnology Progress, Sep. 2007, vol. 23, No. 5, pp. 1017-1022.

* cited by examiner

*Primary Examiner* — Delia Ramirez
(74) *Attorney, Agent, or Firm* — Birch, Stewart, Kolasch & Birch, LLP

(57) ABSTRACT

The present invention relates to a method for the production of hyaluronic acid (HA) in *Bacillus subtilis* and *Escherichia coli* through plasmid vectors wherein the gene is under the control of strong promoter Pgrac, and a system for the selection of stable bacterial strains for the production of high levels of hyaluronic acid.

8 Claims, 6 Drawing Sheets

Expression of HAS1 and TUAD in E. coli TOP-10

Cells with plasmid HT01 incorporated are larger than cells with BS5 (growth difficulties)

Cells with BS5 incorporated are yellower than the parental cells

TuaD expression in E. coli BL21 DE3

*Constitutive expression of hyaluronan synthase (Streptc) in E. coli*

*Bacillus subtilis*
Expression of hyaluronic acid on plates

800N BS5     1012 BS5 (1)     1012 BS5 (2)

When the bacteria are seeded in the presence of 1mM IPTG, they die.
TuaD expressed at high levels is toxic to Bacillus subtilis!

Expression of hyaluronic acid on plates

The large, translucent colonies produce HA

Stability of the plasmid after growth

Chloramphenicol+        Chloramphenicol-

METHOD FOR OBTAINING RECOMBINANT HOST BACTERIAL CELLS THAT PRODUCE HYALURONIC ACID

This application is the National Phase Under 35 U.S.C. §371 of PCT International Application No. PCT/EP2011/065642 which has an International filing date of Sep. 9, 2011, which claims priority to Italian Patent Application No. MI2010A001642 filed on Sep. 9, 2010. The entire contents of all applications listed above are hereby incorporated by reference.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015_10_21_0471_0323PUS1_ST25.txt" created on Oct. 21, 2015, and is 17,029 bytes in size. The sequence listing contained in this .txt file is part of the specification and is hereby incorporated by reference herein in its entirety.

SUBJECT OF THE INVENTION

The present invention discloses a method for the production of hyaluronic acid (HA) in *Bacillus subtilis* and *Escherichia coli* through plasmid vectors wherein the gene is under the control of the strong promoter Pgrac, and a system for the selection of stable bacterial strains, for the production of high levels of HA.

FIELD OF INVENTION

Hyaluronic acid is a natural linear polysaccharide which consists of alternating β-1-4 D-glucoronic acid and β-1-3 N-acetyl glucosamine. Hyaluronic acid is part of the glycosaminoglycan family, and can reach, the molecular weight of $10^7$ Da, with approx. 300000 repeating saccharide units. It is widely distributed in the extracellular matrix of connective tissue and in the epithelium of eukaryotic organisms, where it is located on the cell surface, but can also be synthesised in some prokaryotic organisms, such as those of the *Streptococcus* family. Glucosaminoglycans are ideal joint lubricants, but also perform many other functional roles in tissue repair, adherence, development, cell motility, cancer and angiogenesis. Products based on hyaluronic acid have been developed on the basis of these important characteristics, and are used in orthopaedics, rheumatology and dermatology.

The most common natural sources of HA include rooster combs, the classic material from which HA is extracted, and some bacteria, especially those belonging to the *Streptococcus* family. All these different sources present numerous disadvantages: hyaluronic acid obtained, from rooster combs can, for example, cause allergies in humans because it is of avian origin, while HA from bacterial sources must be free of all the toxins normally present in those bacteria which can cause possibly serious immune/inflammatory reactions. The current industrial HA purification processes therefore comprise many different steps, with a consequent increase in the final costs of manufacturing the raw material. There is consequently a strongly felt need for alternative sources that eliminate all the adverse events described, while maintaining reasonable manufacturing costs. In recent years, biosynthesis pathways for the synthesis of hyaluronic acid have been clarified in detail in numerous organisms. While the genes required for hyaluronic acid synthesis which are present in eukaryotic organisms are distributed throughout the genome, in bacterial systems said genes are often present and organised in operons. For example, in *Streptococcus equi* the operon for hyaluronic acid comprises 5 genes: hasA, hasB, hasC, hasD and hasE. Sometimes, however, the genes are present in two operons: in *Streptococcus equisimilis* one operon with genes hasA, hasB and hasC is present, and another with genes hasC, hasD and hasE. The genes homologous with hasB, hasC, hasD and hasE of the Streptococci are present in many organisms, because they synthesise the enzymes necessary for the synthesis of the precursors of hyaluronic acid, D-glucuronic acid and N acetyl-D glucosamine, which are also the basic constituents of the bacterial walls. In the case of Streptococci, hyaluronan synthase (hasA, which is present in the plasma membrane) is the key enzyme for the final synthesis of hyaluronic acid because it performs two functions: it catalyses the union of D-glucuronic acid and N-acetyl-D-glucosamine, and transports the chain of newly-formed hyaluronic acid out of the cell. The study of the enzymes responsible for hyaluronic acid synthesis has allowed the development of recombinant systems in various organisms, such as *Bacillus subtilis, Lactococcus lactis, Escherichia coli* and *Agrobacterium radiobacter*. The first organism engineered to produce hyaluronic acid was *B. subtilis*, through cloning in its chromosome of an operon that carries the hasA gene from *Streptococcus* (which is missing in *Bacillus*), with the tuaD and gtaB genes of *Bacillus* (corresponding to hasB and hasC of *Streptococcus*), under the control of a constitutive promoter (US2003/175902). In this way a biosynthesis pathway was organised in operons similar to those of *Streptococcus equi*, one of the major natural producers of hyaluronic acid. However, the system thus perfected leads to the industrial production of a hyaluronic acid with a molecular weight of less than 1 MDA, with very low manufacturing yields.

*Bacillus subtilis* is a Gram-positive bacterium, classified as an obligate aerobe, normally found in soil. It is capable of forming a tough, protective endospore which enables the organism to withstand extreme environmental conditions; bacteria of the genus *Bacillus* are consequently among the most widespread microorganisms in nature, with representatives isolated from soil and aquatic environments.

Of all the species, only a very few pathogenic ones are known, including *Bacillus anthracis*, which causes anthrax, *B. thuringiensis*, a pathogen of insects, and *Bacillus cereus*, which causes food poisoning. Conversely, *Bacillus subtilis* is considered to be a GRAS (Generally Regarded As Safe) micro-organism and, being free of endo/exotoxins, is used to manufacture substances used in the food industry (both foodstuffs and drinks), products such as enzymes, antibiotics and insecticides, and in the detergent industry. Attempts to use *Bacillus subtilis* in the production of aminoacids such as tryptophan, histidine and phenylalanine, and vitamins such as biotin, folic acids and riboflavin, have given promising results.

The main source of *Bacillus* species is soil; *B. subtilis* is a prototroph which grows at mesophilic temperatures on defined (including minimal) synthetic media, containing both glucose and other sugars as carbon source.

DETAILED DESCRIPTION OF THE INVENTION

The present invention discloses a method for the production of hyaluronic acid (HA) in *Bacillus subtilis* and *Escherichia coli* through plasmid vectors wherein the genes for the synthesis of the enzymes necessary to the production of HA are under the control of strong promoter Pgrac, and a system for the selection of stable, engineered and secreting bacterial strains, for the production of high amounts of HA having specific weight average molecular weight (in the following indicated also simply with MW).

During the construction in *E. coli* of vectors expressing hyaluronic acid in the form of plasmids, it was discovered that the genes thus introduced (responsible for synthesising hyaluronic acid-producing enzymes) are toxic to the cell when their translation control is a strong constitutive promoter. In fact, in *E. coli* transformed with the hasA and tuaD genes, gene translation of hasA alone leads to a great reduction in the precursors of D-glucuronic acid required for the constitution of the bacterial wall, with the result that the cell dies; whereas gene translation of tuaD alone generates uncontrolled synthesis of D-glucuronic acid which, by acidifying the bacterium and depriving it of glucose (its precursor), causes its death. Conversely, the translation of both genes by bacterial polymerases leads to the synthesis/activation of the two enzymes at different times, because they require different construction times with different procedures and sites of action (for example, hasA is a transmembrane protein with different domains crossing it, so a much longer time is needed for its synthesis and correct folding than for the synthesis/activation of the tuaD enzyme). The cell can only survive when balanced quantities of the precursor enzymes and the enzyme necessary for hyaluronic acid synthesis are present. In this case, the excess D-glucuronic acid, which is toxic at high levels in the cell, is used by hyaluronan synthase (hasA) which, combining it with glucosamine, incorporates it in the nascent hyaluronic acid and exports it from the cell, thus keeping the cell alive.

The Applicant has therefore now surprisingly found that although both hasA and hasB (tuaD) are necessary for hyaluronic acid synthesis, it is essential for the two genes to work in concert, leaving the cell the time required to:
  produce D-glucuronic acid at non-toxic levels and
  trigger the transcription of the hasA gene in such a way that the latter is able to dispose of the high levels of D-glucuronic acid as they progressively accumulate in the cell.

In the present invention, the problems described above have been solved by:
  placing the plasmid genes under the control of an inducible promoter, Pgrac, which uses the repressor lac;
  improving a system of selection of stable, viable, engineered and secreting *B. subtilis* strains, wherein the hasA and tuaD enzymes are present in "balanced" amounts, thus non toxic.

It is therefore object of the present invention a process for the production of hyaluronic acid in *Escherichia coli* or *Bacillus subtilis*, preferably in *Bacillus subtilis*, comprising the following steps:
  (a) culture of bacterial host cells of *Escherichia coli* that constitutively express the lac repressor, or of *Bacillus subtilis* transformed with the grac-lac system, under conditions suitable for producing hyaluronic acid, and in the presence of isopropyl-β-thio-galactopyranoside (IPTG) as inducer, wherein such bacterial host cells are characterised by being transformed with:
    (i) at least one episomal plasmid vector comprising a sequence coding for the enzyme hyaluronan synthase, a sequence coding for the enzyme UDP-glucose dehydrogenase in tandem, under the control of strong inducible promoter Pgrac which uses the lac repressor, or
    (ii) at least one episomal plasmid vector comprising a sequence coding for the enzyme hyaluronan synthase, a sequence coding for the enzyme UDP-glucose dehydrogenase, a sequence coding for the enzyme UDP-glucose pyrophosphorylase and a sequence coding for the enzyme glucose 6 phosphate isomerase, under the control of strong inducible promoter Pgrac which uses the lac repressor;
  (b) recovery of hyaluronic acid from the culture medium:
    wherein said bacterial host cells of *Escherichia coli* or *Bacillus subtilis* transformed with plasmid vector (i) or (ii) capable of producing hyaluronic acid of step a) are pre-selected in the plate on IPTG gradient.

The Applicant preferably used *B. subtilis* for its transformation with the episomal plasmid containing the genes for HA synthesis, because it presents various advantages as host for the expression of heterologous DNA:
  the HA produced is easily secreted;
  it is free of exotoxins and endotoxins, unlike gram-negative bacteria. Preferably said bacterial host cells of *B. subtilis* is pertain to WB800N or 1012 strains.

In particular, when bacterial host cells of *B. subtilis* are used, the episomal plasmid (i) or (ii) further comprises a sequence coding for the lac repressor.

The grac-lac system transferred, to *B. subtilis* (and *E. coli*) with episomal plasmid, controls the expression of the genes responsible for synthesis of the HA biosynthesis pathway (cloned in the same episomal plasmid), and guarantees very high activity and selectivity of gene transcription, leading to high production of the recombinant proteins required for the synthesis of hyaluronic acid. The final yield of the desired product will be very high, much higher than that obtained with *B. subtilis*, where the operon system is cloned on the chromosome of the bacterium and is under the control of non-inducible constitutive promoters.

In fact, the system described above is inducible: it is introduced artificially into the bacterium and activated by the Applicant by adding substances such as IPTG (isopropylthiogalactoside) in quantities of between 0.005 and 10 mM, preferably of between 0.01 and 5 mM, and more preferably between 0.4 and 1 mM.

The grac-lac system comprises the Pgrac promoter with the gene sequence LacI for the synthesis not inducible of the lac repressor protein, Pgrac is an artificial promoter comprising groE promoter, lacO operator and a ribosome binding site. IPTG (when added) determines the detachment of the lac repressor protein from the lacO operator site, so that the *B. subtilis* polymerase can recognise the groE promoter and starts the transcription of hasA and tuaD genes.

In this way, by modulating with IPTG the induction of the above disclosed system, the Applicant can control the synthesis of the whole biosynthesis process for the production of HA and obtain the wished weight average molecular weights, comprised in a range of from 100 KD to above 2 MD, with high HA yields. More particularly, when the process according to the invention uses bacterial host cells of *B. subtilis* and fermentation time is comprised of from 80 to 160 hours, it is possible to obtain HA having a weight average MW comprised in the range 100-500 KD; when fermentation time is comprised of from 40 to 80 hours, it is possible to obtain HA having a weight average MW comprised in the range 500-1000 KD; when fermentation lime is comprised of from 12 to 40 hours, it is possible to obtain HA having a weight average MW comprised in the range $1 \times 10^6$-$2 \times 10^6$ D.

In a preferred embodiment of the present invention, the sequence coding for the enzyme hyaluronan synthase (hasA) is obtained from a *Streptococcus* strain, preferably from *Streptococcus zooepidemicus*, and the sequences coding for enzymes UDP-glucose dehydrogenase (hasB or tuaD), UDP-glucose pyrophosphorylase (hasC or gtaB) and glucose 6 phosphate isomerase (hasE or pgi), are derived from *B. subtilis*.

According to a particularly preferred embodiment of the present invention, the sequences coding for enzymes hyaluronan synthase, UDP-glucose dehydrogenase, UDP-glucose pyrophosphorylase and glucose 6 phosphate isomerase include an upstream Shine-Dalgarno sequence.

Even more preferably, said plasmid vector (i) comprises or consists of the nucleotide sequence as defined in SEQ ID NO:1.

The subsequent purification of the HA secreted, will be extremely simple, with the result that the industrial production process will be much cheaper than the process according to the state of the art.

A further object of the present invention are plasmid vectors containing the two genes hasA and tuaD or the four genes hasA, tuaD, gtaB and pgi (corresponding to hasE), preferably plasmid vectors with two genes hasA and tuaD, under control of strong inducible promoter Pgrac, which allow the production of hyaluronic acid with high yields according to the methodology described above. In a particularly preferred embodiment of the present invention, said plasmid vector also includes a sequence coding for the lac repressor. Preferably, said sequence coding for enzyme hyaluronan synthase is gene hasA from *Streptococcus zooepidemicus* and said sequence coding for enzyme UDP-glucose dehydrogenase is gene tuaD from *Bacillus subtilis*. In a particularly preferred form, the plasmid vector comprises or consists of SEQ ID NO: 1.

Preferably, the sequences coding for the hyaluronan synthase enzyme, UDP-glucose dehydrogenase, UDP-glucose pyrophosphorylase and glucose 6 phosphate isomerase include an upstream Shine-Dalgarno sequence. These vectors can also be constructed so as to contain any other gene relating to the biosynthesis of hyaluronic acid. Unlike those available to date, the starting plasmid is small, which allows engineering of the entire hyaluronic acid biosynthesis pathway (i.e. the two genes hasA and tuaD or the four genes hasA, tuaD, gtaB and pgi) in a single plasmid, which is called pHT01hasAtuaD or pHT01hasAtuaDgtaBpgi here, making the invention described economically advantageous and successfully applicable on an industrial scale. A further subject of the present invention is consequently plasmid pHT01hasAtuaD and plasmid pHT01hasAtoaPgtaBpgi. For the high yield synthesis of HA having the wished high weight average molecular weight, the Applicant has demonstrated that it is preferred the engineering of *B. subtilis* with plasmid pHT01hasAtuaD.

The present invention also relates to a method and relative system for the production/construction of bacterial strains, transformed with plasmid containing the entire hyaluronic acid biosynthesis pathway, and the selection of stable, viable, replicating and HA-secreting bacterial strains.

Said method comprises the following steps:
Cloning of the tuaD gene (UDP-glucose dehydrogenase) from *Bacillus Subtilis*,
Cloning of the hasA (hyaluronan synthase) gene from *Streptococcus zooepidemicus*
Construction of plasmid pGEM4hasA and subsequently of plasmid pHT01hasA
Construction of plasmid with the tuaD gene following hasA
Construction of plasmid pHT01hasAtuaD, which will be referred to as pBS5
Transformation of plasmid pBS5 into *Bacillus subtilis* or *E. coli*
Selection of cells secreting hyaluronic acid through IPTG gradient
Selection of stable, viable and secreting cells.

The present invention will be now disclosed by way of example but not of limitation, according to preferred embodiments with particular reference to the attached figures, wherein.

Figure 4:
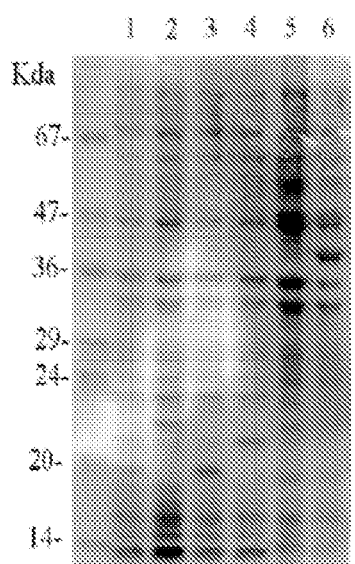
Figure 5:
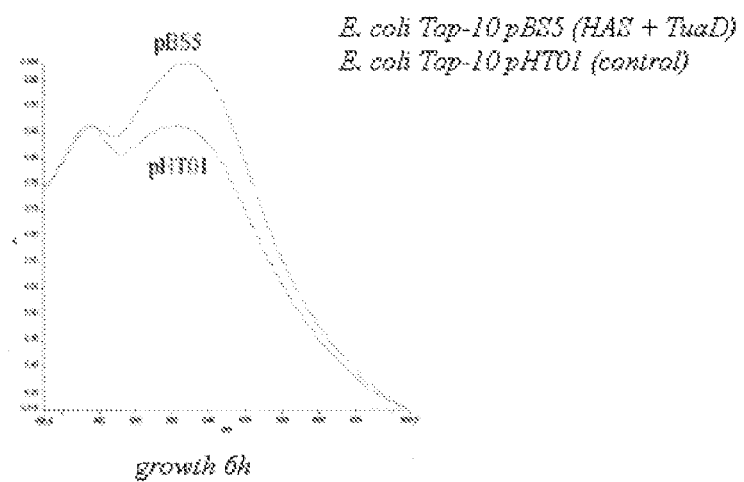
Figure 6:
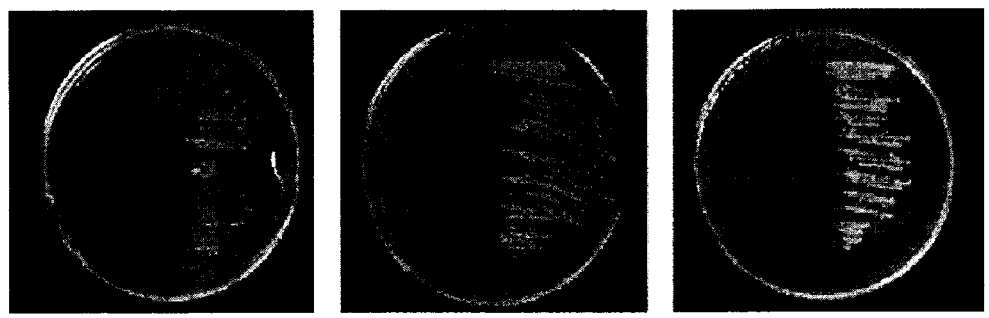
Figure 7:
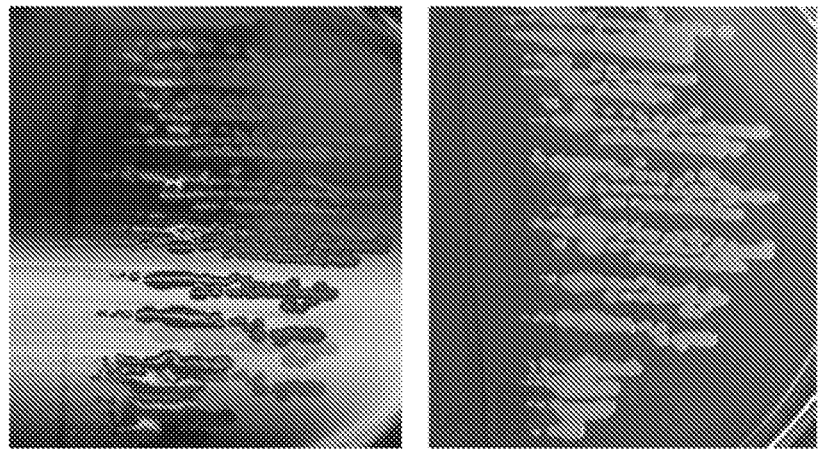
Figure 8:
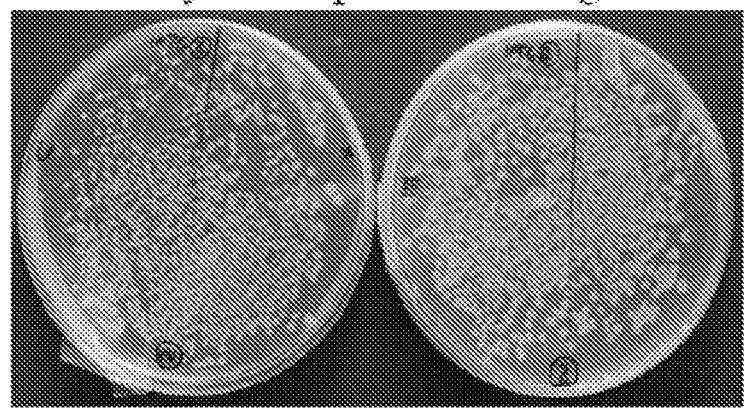

FIG. 4 shows the analysis in gel electrophoresis of the constitutive expression of hyaluronan synthase (Strept) in *E. coli*; the encoded protein designated SeHAS is 417 amino acids long (calculated molecular weight 47,778; calculated PI 9.1) and is the smallest member of the HAS family identified thus far; the enzyme migrates anomalously fast in SDS polyacrylamide gel electrophoresis (about 42000 Da);

FIG. 5 shows the comparison between the profiles of expression of HA in strains of *E. Coli* TOP10+pBS5 (hasA+tuaD) and TOP10+pHT01 (control) through carbazole analysis of glucuronic acid at 530 nm;

FIG. 6 shows the comparison in plates among the expression of glucuronic acid in strains of *Bacillus subtilis* WB800N and 1012 transformed with pBS5; when bacteria are seeded in presence of IPTG 1 mM, they die because tuaD expressed at high amounts in *B. subtilis* is toxic;

FIG. 7 shows the expression of glucuronic acid in *Bacillus subtilis* in plates wherein large and translucent colonies produce HA;

FIG. 8 shows the results of plating assays to verify the stability of plasmid after 24 hours of cells growth in presence of IPTG and saccharose and in presence or absence of chloramphenicol.

The following examples describe the various steps required for the embodiment of the process of production of HA according to the present invention, by way of example but not of limitation.

Example 1

Cloning of the tuaD Gene (UDP-Glucose Dehydrogenase) from *Bacillus Subtilis*

The sequence of the tuaD gene, which is 9300 bp long in *B. subtilis*, is present in the databases as access number AF015609; it codes for the operon which leads to teichuronic acid synthesis and comprises 8 genes, tuaABCDEFGH. In our case the gene of interest tuaD falls between the bases 3582-4984 bp. Software analysis for restriction enzymes indicates that the restriction sites ClaI, EcoRI, PstI, HindIII and SphI are present, and therefore cannot be used for cloning. The start codon is not a methionine but a valine; in the present invention it was replaced with the codon for methionine, which translates the protein much more efficiently. Two oligonucleotide primers synthesised with the following sequence were used to recover this sequence:

```
5' atgaaaaaatagctgtcattggaacag 3'   (SEQ ID NO: 2)
and
5' ttataaattgtcgttcccaagtct 3'      (SEQ ID NO: 3)
```

The genomic DNA from *B. subtilis* (strain 168) was obtained with the Qiagen extraction kit. With 32 cycles of PCR, using DNA from *B. subtilis* as template and the two said oligonucleotides, an amplificate of the expected molecular weight was obtained. The amplificate obtained was tested for the presence of restriction enzyme EcoRI. After cutting with this enzyme in 1% agarose gel, two bands of DNA weighing 470 bp and 920 bp are present, which correspond to those expected. To clone the tuaD gene in an expression vector, two other oligonucleotides with the following sequence were synthesised:

```
                                        (SEQ ID NO: 4)
    5' gctggatccatgaaaaaatagctgtcattgg 3'
and
                                        (SEQ ID NO: 5)
    5' ctcgctagcttataaattgacgcttcccaag 3'
``` so as to insert said sequence between the restriction sites BamHI and NheI in the expression vector, plasmid pRSETB (INVITROGEN).

A Shine-Dalgarno (SD) sequence needs to be introduced into the tuaD gene upstream of the 5' end of the gene to allow efficient recognition by the bacterial RNA polymerase. For this purpose the DNA was amplified with the following oligonucleotides:

```
                                        (SEQ ID NO: 6)
    5' cgacatatgaaaaaatagctgtcattgg 3'
and
                                        (SEQ ID NO: 7)
    5' ctcgctagcttataaattgacgcttcccaag 3'.
```

They contain in 5' two restriction sites NdeI and NheI which allow its cloning in vector pRSET B between the same sites. In this way, a particularly efficient sequence SD, which is necessary for RNA polymerase in order to synthesise the protein, is present upstream of the NdeI restriction site of plasmid pRSET B. Restriction site XbaI, which will be required for the subsequent clonings, is also present even before said sequence. The vector created, pRSET B, was therefore called pRSEtuaD.

Thus in this plasmid, the sequence coding for tuaD falls between the restriction sites NdeI and NheI; restriction site XbaI, which is necessary for the subsequent cloning, is present before and upstream of said plasmid, and other restriction sites, including BamHI-BglII-XhoI, are present behind the tuaD gene.

The diagram below summarises the sites of interest present in plasmid pRSEtuaD

XbaI-NdeI - - - tuaD - - - NheI-BamHI-BglI-XhoI

Figure 1:
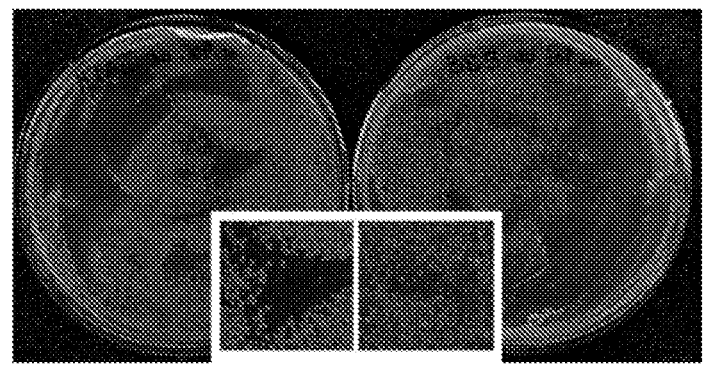
FIG. 1 shows a comparison in plates between the growth of cells *E. coli* TOP10, incorporating plasmid pHT01 (control) and cells *E. coli* TOP10, incorporating pBS5 (hasA+tuaD)

The plasmid described is an expression vector which also functions in *E. coli*, because the gene is under the control of the T7 promoter; if it is transformed to bacterial cells BL21 DE3, which are able to transcribe T7 RNA polymerase, it therefore enables them to express the tuaD gene. After induction with 1 mM of IPTG the transfected cells are able to produce the protein of the expected molecular weight, but not hyaluronic acid. The construction is particularly efficient because the level of expression is very high. The sizes of the colonies which carry plasmid pRSEtuaD are very small compared with the control cells (FIG. 1), which demonstrates the toxicity of the tuaD gene. This cloning is difficult precisely because it is apparently difficult for the colonies to grow; the particularly high level of expression of this protein probably drains the glucose available for uncontrolled synthesis of D-glucuronic acid, thus depriving the cell of its main energy source. The cells in which the tuaD synthesis is induced with IPTG are unable to survive for a long time, so the gene product is toxic.

Figure 2:
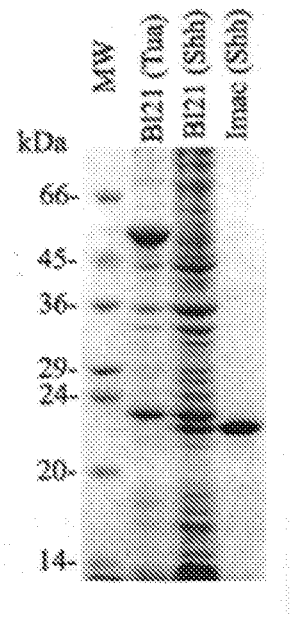
FIG. 2 shows the gel analysis of the expression of gene tuaD in *E. coli* BL21 DE3.

In conclusion, the tuaD gene was isolated and cloned in a plasmid and the sequence proved correct. The gene expressed in *E. coli* is able to produce a protein of the expected molecular weight corresponding to that described for tuaD (54 kDa, FIG. 2); however, in the absence of hyaluronan synthase, these cells are unable to produce significant amounts of hyaluronic acid, and the consequent accumulation of glucuronate is toxic to the cell.

Example 2

Cloning of the hasA (Hyaluronan Synthase) Gene from *Streptococcus zooepidemicus*

The gene sequence for hyaluronan synthase is present in the databases with access number AY173078, and is 3552 bp long; the sequence coding for the protein is between bases 1 and 1254. The restriction sites HindIII and StuI are present, in this sequence, and therefore cannot be used for cloning, but can be used to verify the cloning. Two oligonucleotides for use with PCR were designed and synthesised to recover the coding sequence:

```
                                        (SEQ ID NO: 8) e
    5' atgagaacattaaaaaacctcataac 3'

(SEQ ID NO: 9)
    5' taataattttttacgtgttccccag 3'
```

The genomic DNA from the bacterium *Streptococcus zooepidemicus* was recovered with the Qiagen extraction kit. The 1254 bp coding sequence was recovered with PCR. The expected amplificate of the correct dimensions was controlled with restriction enzyme HindIII, and gave rise to two bands of approx. 100 bp and 1150 bp which correspond to the expected cut.

Example 3

Construction of Expression Plasmid pHT01hasA for *Bacillus subtilis*

Figure 3:
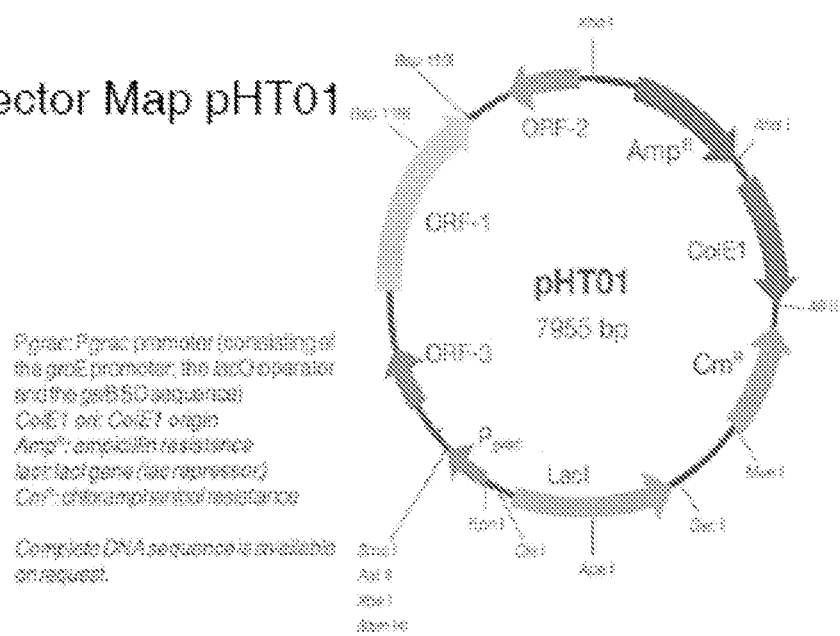
FIG. 3 (SEQ ID NO: 12) illustrates the vector map pHT01 comprising Pgrac promoter consisting of the groE promoter, the lacO operator and the gsB SD sequence; the replication origin ColE1; $Amp^R$ ampicillin resistance gene; lacI gene (lacI repressor); and $Cm^R$ chloramphenicol resistance gene.

To clone said gene in expression vector pHT01. (Mobitec—FIG. 3) containing the gene promoter-represser system grac-lac, the above-mentioned sequence must be cloned between restriction sites BamHI and XbaI. Two other oligonucleotides with the following sequence were created for this purpose:

```
                                        (SEQ ID NO: 10) e
    5' ggaggatccatgagaacattaaaaaacctcat 3'

(SEQ ID NO: 11)
    5' cagtctagattataataattttttacgtgtcc 3'
```

In the first oligonucleotide, restriction site BamHI was created near 5', while in the second oligonucleotide, restriction site XbaI was created, again at 5'. The amplificate obtained through these two oligonucleotides was cloned in plasmid pGEM4Z (PROMEGA) between restriction sites BamHI and XhaI to give plasmid pGEM4hasA.

The DNA sequence between said two restriction sites was analysed with an ABI 7000 sequencer, and proved correct.

HindIII-BamHI - - - hasA - - - XbaI-SalI

The plasmid was checked for expression of the recombinant protein in *E. coli*, and presented a molecular weight of approx. 42 kDa (which agrees with the weight reported for that protein in the literature, although it has a theoretical molecular weight of 47.778 kDa, FIG. 4).

To clone said sequence between restriction sites BamHI and XbaI of vector pHT01, plasmid pGEM4hasA was cut in sites BamHI and XbaI, and the 1240 bp band was cloned in the same sites as plasmid pHT01 to obtain plasmid pHT01hasA. This plasmid is unable to produce significant quantities of hyaluronic acid because it lacks the tuaD gene. This proves that the presence of hasA alone is not sufficient to express significant amounts of HA.

Example 4

Construction of Expression Plasmid pHT01hasA-tuaD for *Bacillus subtilis*

With this construction, the hasA gene is placed in tandem with the tuaD gene under the control of inducible promoter Pgrac present in plasmid pHT01 (Mobitec). Plasmid pGEM4hasA (described in the previous example) was used as vector for this purpose, as it already contains the hasA gene. Said plasmid was cut in sites XbaI and SalI, while the sequence of the tuaD gene was cut by plasmid pRESEtuaD in sites XbaI and XhoI and then cloned in the same sites (XhoI and SalI are compatible).

pGEM4hasA
HindIII-BamHI - - - hasA - - - XbaI-SalI
pRSEtuaD
XbaI-NdeI - - - tuaD - - - NheI-BamHI-BglI-XhoI
obtaining this sequence:
HindIII-BamHI - - - hasA - - - XbaI-NdeI - - - tuaD - - - NheI-BamHI-BglI-XhoI At this point the hasA gene is in tandem with the tuaD gene; fragment BamHI - - - NheI, which is obtained from the plasmid by cutting with said restriction enzymes, contains the hasA gene and the tuaD gene in tandem. The fragment was then cloned in vector pHT01 between restriction sites BamHI and XbaI (XbaI is compatible with NheI), giving rise to plasmid pBS5, the complete, controlled sequence of which is set out below:

```
                                                        (SEQ ID NO: 1)
   0  TTAAGTTATTGGTATGACTGGTTTTAAGCGCAAAAAAAGTTGCTTTTTCGTACCTATTAA
  60  TGTATCGTTTTAGAAAACCGACTGTAAAAAGTACAGTCGGCATTATCTCATATTATAAAA
 120  GCCAGTCATTAGGCCTATCTGACAATTCCTGAATAGAGTTCATAAACAATCCTGCATGAT
 180  AACCATCACAAACAGAATGATGTACCTGTAAAGATAGCGGTAAATATATTGAATTACCTT
 240  TATTAATGAATTTTCCTGCTGTAATAATGGGTAGAAGGTAATTACTATTATTATTGATAT
 300  TTAAGTTAAACCCAGTAAATGAAGTCCATGGAATAATAGAAAGAGAAAAAGCATTTTCAG
 360  GTATAGGTGTTTTGGGAAACAATTTCCCCGAACCATTATATTTCTCTACATCAGAAAGGT
 420  ATAAATCATAAAACTCTTTGAAGTCATTCTTTACAGGAGTCCAAATACCAGAGAATGTTT
 480  TAGATACACCATCAAAAATTGTATAAAGTGGCTCTAACTTATCCCAATAACCTAACTCTC
 540  CGTCGCTATTGTAACCAGTTCTAAAAGCTGTATTTGAGTTTATCACCCTTGTCACTAAGA
 600  AAATAAATGCAGGGTAAAATTTATATCCTTCTTGTTTTATGTTTCGGTATAAAACACTAA
 660  TATCAATTTCTGTGGTTATACTAAAAGTCGTTTGTTGGTTCAAATAATGATTAAATATCT
 720  CTTTTCTCTTCCAATTGTCTAAATCAATTTTATTAAAGTTCATTTGATATGCCTCCTAAA
 780  TTTTTATCTAAAGTGAATTTAGGAGGCTTACTTGTCTGCTTTCTTCATTAGAATCAATCC
 840  TTTTTTAAAAGTCAATATTACTGTAACATAAATATATATTTTAAAAATATCCCACTTTAT
 900  CCAATTTTCGTTTGTTGAACTAATGGGTGCTTTAGTTGAAGAATAAAGACCACATTAAAA
 960  AATGTGGTCTTTTGTGTTTTTTTAAAGGATTTGAGCGTAGCGAAAAATCCTTTTCTTTCT
1020  TATCTTGATAATAAGGGTAACTATTGCCGATCGTCCATTCCGACAGCATCGCCAGTCACT
1080  ATGGCGTGCTGCTAGCGCCATTCGCCATTCAGGCTGCGCAACTGTTGGGAAGGGCGATCG
1140  GTGCGGGCCTCTTCGCTATTACGCCAGCTGGCGAAAGGGGATGTGCTGCAAGGCGATTA
                                                              EcoRI
1200  AGTTGGGTAACGCCAGGGTTTTCCCAGTCACGACGTTGTAAAACGACGGCCAGTGAATTC
1260  GAGCTCAGGCCTTAACTCACATTAATTGCGTTGCGCTCACTGCCCGCTTTCCAGTCGGGA
1320  AACCTGTCGTGCCAGCTGCATTAATGAATCGGCCAACGCGCGGGGAGAGGCGGTTTGCGT
1380  ATTGGGCGCCAGGGTGGTTTTTCTTTTCACCAGTGAGACGGGCAACAGCTGATTGCCCTT
1440  CACCGCCTGGCCCTGAGAGAGTTGCAGCAAGCGGTCCACGCTGGTTTGCCCCAGCAGGCG
1500  AAAATCCTGTTTGATGGTGGTTGACGGCGGGATATAACATGAGCTGTCTTCGGTATCGTC
```

-continued

```
1560 GTATCCCACTACCGAGATATCCGCACCAACGCGCAGCCCGGACTCGGTAATGGCGCGCAT
1620 TGCGCCCAGCGCCATCTGATCGTTGGCAACCAGCATCGCAGTGGGAACGATGCCCTCATT
1680 CAGCATTTGCATGGTTTGTTGAAAACCGGACATGGCACTCCAGTCGCCTTCCCGTTCCGC
1740 TATCGGCTGAATTTGATTGCGAGTGAGATATTTATGCCAGCCAGCCAGACGCAGACGCGC
1800 CGAGACAGAACTTAATGGGCCCGCTAACAGCGCGATTTGCTGSTGACCCAATGCGACCAG
1660 ATGCTCCACGCCCAGTCGCGTACCGTCTTCATGGGAGAAAATAATACTGTTGATGGGTGT
1920 CTGGTCAGAGACATCAAGAAATAACGCCGGAACATTAGTGCAGGCAGCTTCCACAGCAAT
1980 GGCATCCTGGTCATCCAGCGGATAGTTAATGATCAGCCCACTGACGCGTTGCGCGAGAAG
2040 ATTGTGCACCGCCGCTTTACAGGCTTCGACGCCGCTTCGTTCTACCATCGACACCACCAC
2100 GCTGGCACCCAGTTGATCGGCGCGAGATTTAATCGCCGCGACAATTTGCGACGGCGCGTG
2160 CAGGGCCAGACTGGAGGTGGCAACGCCAATCAGCAACGACTGTTTGCCCGCCAGTTGTTG
2220 TGCCACGCGGTTGGGAATGTAATTCAGCTCCGCCATCGCCGCTTCCACTTTTTCCCGCGT
2280 TTTCGCAGAAACGTGGCTGGCCTGGTTCACCACGCGGGAAACGGTCTGATAAGAGACACC
2340 GGCATACTCTGCGACATCGTATAACGTTACTGGTTTCATCAAAATCGTCTCCCTCCGTTT
2400 GAATATTTGATTGATCGTAACCAGATGAAGCACTCTTTCCACTATCCCTACAGTGTTATG
2460 GCTTGAACAATCACGAAACAATAATTGGTACGTACGATCTTTCAGCCGACTCAAACATCA
2520 AATCTTACAAATGTAGTCTTTGAAAGTATTACATATGTAAGATTTAAATGCAACCGTTTT
2580 TTCGGAAGGAAATGATGACCTCGTTTCCACCGGAATTAGCTTGGTACCAGCTATTGTAAC
2640 ATAATCGGTACGGGGGTGAAAAAGCTAACGGAAAAGGGAGCGGAAAAGAATGATGTAAGC
2700 GTGAAAAATTTTTTATCTTATCACTTGAAATTGGAAGGGAGATTCTTTATTATAAGAATT
                                                          BamHI
2760 GTGGAATTGTGAGCGGATAACAATTCCCAATTAAAGGAGGAAGGATCCATGAGAACATTA
   1                                                       M R T L
2820 AAAAACCTCATAACTGTTGTGGCCTTTAGTATTTTTTGGGTACTGTTGATTTACGTCAAT
   1 K  N  L  I  T  V  V  A  F  S  I  F  W  L  L  I  Y  V  N
                                    HindIII
2880 GTTTATCTCTTTGGTGCTAAAGGAAGCTTGTCAATTTATGGCTTTTTGCTGATAGCTTAC
   1 V  Y  L  F  G  A  K  G  S  L  S  I  Y  G  F  L  L  I  A  Y
2940 CTATTAGTCAAAATGTCCTTATCCTTTTTTACAAGCCATTTAAGGGAAGGGCTGGGCAA
   1 L  L  V  K  M  S  L  S  F  F  Y  K  P  F  K  G  R  A  G  Q
3000 TATAAGGTTGCAGCCATTATTCCCTCTTATAACGAAGATGCTGAGTCATTGCTAGAGACC
   1 Y  K  V  A  A  I  I  P  S  Y  N  E  D  A  E  S  L  L  E  T
3060 TTAAAAAGTGTTCAGCAGCAAACCTATCCCCTAGCAGAAATTTATGTTGTTGACGATGGA
   1 L  K  S  V  Q  Q  Q  T  Y  P  L  A  E  I  Y  V  V  D  D  G
3120 AGTGCTGATGAGACAGGTATTAAGCGCATTGAAGACTATGTGCGTGACACTGGTGACCTA
   1 S  A  D  E  T  G  I  K  R  I  E  D  Y  V  R  D  T  G  D  L
3180 TCAAGCAATGTCATTGTTCACCGGTCAGAAAAAAATCAAGGAAAGCGTCATGCACAGGCC
   1 S  S  N  V  I  V  H  R  S  E  K  N  Q  G  K  R  H  A  Q  A
3240 TGGGCCTTTGAAAGATCAGACGCTGATGTCTTTTTGACCGTTGACTCAGATACTTATATC
   1 W  A  F  E  R  S  D  A  D  V  F  L  T  V  D  S  D  T  Y  I
3300 TACCCTGATGCTTTAGAGGAGTTGTTAAAAACCTTTAATGACCCAACTGTTTTTGCTGCG
   1 Y  P  D  A  L  E  E  L  L  K  T  F  N  D  P  T  V  F  A  A
3360 ACGGGTCACCTTAATGTCAGAAATAGACAAACCAATCTCTTAACACGCTTGACAGATATT
   1 T  G  H  L  N  V  R  N  R  Q  T  N  L  L  T  R  L  T  D  I
3420 CGCTATGATAATGCTTTTGGCGTTGAACGAGCTGCCCAATCCGTTACAGGTAATATTCTC
   1 R  Y  D  N  A  F  G  V  E  R  A  A  Q  S  V  T  G  N  I  L
3480 GTTTGCTCAGGCCCGCTTAGCGTTTACAGACGCGAGGTGGTTGTTCCTAACATAGATAGA
   1 V  C  S  G  P  L  S  V  Y  R  R  E  V  V  V  P  N  I  D  R
```

```
                       -continued
3540 TACATCAACCAGACCTTCCTGGGTATTCCTGTAAGTATCGGTGATGACAGGTGCTTGACC
   1  Y  I  N  Q  T  F  L  G  I  P  V  S  I  G  D  D  R  C  L  T 3600 AACTATGCAACTGATTTAGGAAAGACTGTTTATCAATCCACTGCTAAATGTATTACAGAT
   1  N  Y  A  T  D  L  G  K  T  V  Y  Q  S  T  A  K  C  I  T  D 3660 GTTCCTGACAAGATGTCTACTTACTTGAAGCAGCAAAACCGCTGGAACAAGTCCTTCTTT
   1  V  P  D  K  M  S  T  Y  L  K  Q  Q  N  R  W  N  K  S  F  F 3720 AGAGAGTCCATTATTTCTGTTAAGAAAATCATGAACAATCCTTTTGTAGCCCTATGGACC
   1  R  E  S  I  I  S  V  K  K  I  M  N  N  P  F  V  A  L  W  T 3780 ATACTTGAGGTGTCTATGTTTATGATGCTTGTTTATTCTGTGGTGGATTTCTTTGTAGGC
   1  I  L  E  V  S  M  F  M  M  L  V  Y  S  V  V  D  F  F  V  G 3840 AATGTCAGAGAATTTGATTGGCTCAGGGTTTTGGCCTTTCTGGTGATTATCTTCATTGTT
   1  N  V  R  E  F  D  W  L  R  V  L  A  F  L  V  I  I  F  I  V 3900 GCTCTTTGTCGTAATATTCACTATATGCTTAAGCACCCGCTGTCCTTCTTGTTATCTCCG
   1  A  L  C  R  N  I  H  Y  M  L  K  H  P  L  S  F  L  L  S  P 3960 TTTTATGGGGTACTGCATTTGTTTGTCCTACAGCCCTTGAAATTGTATTCTCTTTTTACT
   1  F  Y  G  V  L  H  L  F  V  L  Q  P  L  K  L  Y  S  L  F  T
                                                      XbaI 4020 ATTAGAAATGCTGACTGGGGAACACGTAAAAAATTATTATAATCTAGAAATAATTTTGTT
   1  I  R  N  A  D  W  G  T  R  K  K  L  L 4080 TAACTTTAAGAAGGAGATATACATATGAAAAAAATAGCTGTCATTGGAACAGGTTATGTA
   1                          M  K  K  I  A  V  I  G  T  G  Y  V 4140 GGACTCGTATCAGGCACTTGCTTTGCGGAGATCGGCAATAAAGTTGTTTGCTGTGATATC
   1  G  L  V  S  G  T  C  F  A  E  I  G  N  K  V  V  C  C  D  I 4200 GATGAATCAAAAATCAGAAGCCTGAAAAATGGGGTAATCCCAATCTATGAACCAGGGCTT
   1  D  E  S  K  I  R  S  L  K  N  G  V  I  P  I  Y  E  P  G  L 4260 GCAGACTTAGTTGAAAAAAATGTGCTGGATCAGCGCCTGACCTTTACGAACGATATCCCG
   1  A  D  L  V  E  K  N  V  L  D  Q  R  L  T  F  T  N  D  I  P 4320 TCTGCCATTCGGGCCTCAGATATTATTTATATTGCAGTCGGAACGCCTATGTCCAAAACA
   1  S  A  I  R  A  S  D  I  I  Y  T  A  V  G  T  P  M  S  K  T 4380 GGTGAAGCTGATTTAACGTACGTGAAAGCGGCGGCGAAAACAATCGGTGAGCATCTTAAC
   1  G  E  A  D  L  T  Y  V  K  A  A  A  K  T  I  G  E  H  L  N 4440 GGCTACAAAGTGATCGTAAATAAAAGCACAGTGCCGGTTGGAACAGGGAAACTGGTGCAA
   1  G  Y  K  V  I  V  N  K  S  T  V  P  V  G  T  G  K  L  V  Q
     EcoRI 4500 TCTATCGTTCAAAAAGCCTCAAAGGGGAGATACTCATTTGATGTTGTATCTAACCCTGAA
   1  S  I  V  Q  K  A  S  K  G  R  Y  S  F  D  V  V  S  N  P  E 4560 TTCCTTCGGGAAGGGTCAGCGATTCATGACACGATGAATATGGAGCGTGCCGTGATTGGT
   1  F  L  R  E  G  S  A  I  H  D  T  M  N  M  E  R  A  V  I  G 4620 TCAACAAGTCATAAAGCCGCTGCCATCATTGAGGAACTTCATCAGCCATTCCATGCTCCT
   1  S  T  S  H  K  A  A  A  I  I  E  E  L  H  Q  P  F  H  A  P 4680 GTCATTAAAACAAACCTAGAAAGTGCAGAAATGATTAAATACGCGGCGAATGCATTTCTG
   1  V  I  K  T  N  L  E  S  A  E  M  I  K  Y  A  A  N  A  F  L 4740 GCGACAAAGATTTCCTTTATCAACGATATCGCAAACATTTGTGAGCGAGTCGGCGCAGAC
   1  A  T  K  I  S  F  I  N  D  I  A  N  I  C  E  R  V  G  A  D 4800 GTTTCAAAAGTTGCTGATGGTGTTGGTCTTGACAGCCGTATCGGCAGAAAGTTCCTTAAA
   1  V  S  K  V  A  D  G  V  G  L  D  S  R  I  G  R  K  F  L  K 4860 GCTGGTATTGGATTCGGCGGTTCATGTTTTCCAAAGGATACAACCGCGCTGCTTCAAATC
   1  A  G  I  G  F  G  G  S  C  F  P  K  D  T  T  A  L  L  Q  I 4920 GCAAAATCGGCAGGCTATCCATTCAAGCTCATCGAAGCTGTCATTGAAACGAACGAAAAG
   1  A  K  S  A  G  Y  P  F  K  L  I  E  A  V  I  E  T  N  E  K 4980 CAGCGTGTTCATATTGTAGATAAACTTTTGACTGTTATGGGAAGCGTCAAAGGGAGAACC
   1  Q  R  V  H  I  V  D  K  L  L  T  V  M  G  S  V  K  G  R  T 5040 ATTTCAGTCCTGGGATTAGCCTTCAAACCGAATACGAACGATGTGAGATCCGCTCCAGCG
   1  I  S  V  L  G  L  A  F  K  P  N  T  N  D  V  R  S  A  P  A
```

```
5100 CTTGATATTATCCCAATGCTGCAGCAGCTGGGCGCCCATGTAAAAGCATACGATCCGATT
   1   L  D  I  I  P  M  L  Q  Q  L  G  A  H  V  K  A  Y  D  P  I
                        HindIII 5160 GCTATTCCTGAAGCTTCAGCGATCCTTGGCGAACAGGTCGAGTATTACACAGATGTGTAT
   1   A  I  P  E  A  S  A  I  L  G  E  Q  V  E  Y  Y  T  D  V  Y 5220 GCTGCGATGGAAGACACTGATGCATGCCTGATTTTAACGGATTGGCCGGAAGTGAAAGAA
   1   A  A  M  E  D  T  D  A  C  L  I  L  T  D  W  P  E  V  K  E 5280 ATGGAGCTTGTAAAAGTGAAAACCCTCTTAAAACAGCCAGTCATCATTGACGGCAGAAAT
   1   M  E  L  V  K  V  K  T  L  L  K  Q  P  V  I  I  D  G  R  N 5340 TTATTTTCACTTGAAGAGATGCAGGCAGCCGGATACATTTATCACTCTATCGGCCGTCCC
   1   L  F  S  L  E  E  M  Q  A  A  G  Y  I  Y  H  S  I  G  R  P 5400 GCTGTTCGGGGAACGGAACCCTCTGACAAGTATTTTCCGGGCTTGCCGCTTGAAGAATTG
   1   A  V  R  G  T  E  P  S  D  K  Y  F  P  G  L  P  L  E  E  L
                                    Nhe/XbaI        SmaI 5460 GCTAAAGACTTGGGAAGCGTCAATTTATAAGCTAGAGTCGACGTCCCCGGGGCAGCCCGC
   1   A  K  D  L  G  S  V  N  L

5520 CTAATGAGCGGGCTTTTTTCACGTCACGCGTCCATGGAGATCTTTGTCTGCAACTGAAAA

5580 GTTTATACCTTACCTGGAACAAATGGTTGAAACATACGAGGCTAATATCGGCTTATTAGG

5640 AATAGTCCCTGTACTAATAAAATCAGGTGGATCAGTTGATCAGTATATTTTGGACGAAGC

5700 TCGGAAAGAATTTGGAGATGACTTGCTTAATTCCACAATTAAATTAAGGGAAAGAATAAA

5760 GCGATTTGATGTTCAAGGAATCACGGAAGAAGATACTCATGATAAAGAAGCTCTAAAACT

5820 ATTCAATAACCTTACAATGGAATTGATCGAAAGGGTGGAAGGTTAATGGTACGAAAATTA
                                                HindIII

5880 GGGCATCTACCTAGAAAGCCACAAGGCGATAGGTCAAGCTTAAAGAACCCTTACATGGAT

5940 CTTACAGATTCTGAAAGTAAAGAAACAACAGAGGTTAAACAAACAGAACCAAAAAGAAAA

6000 AAAGCATTGTTGAAAACAATGAAAGTTGATGTTTCAATCCATAATAAGATTAAATCGCTG
                        EcoRI

6060 CACGAAATTCTGGCAGCATCCGAAGGGAATTCATATTACTTAGAGGATACTATTGAGAGA

6120 GCTATTGATAAGATGGTTGAGACATTACCTGAGAGCCAAAAAACTTTTTATGAATATGAA

6180 TTAAAAAAAGAACCAACAAAGGCTGAGACAGACTCCAAACGAGTCTGTTTTTTTAAAA

6240 AAATATTAGGAGCATTGAATATATATTAGAGAATTAAGAAAGACATGGGAATAAAAATAT

6300 TTTAAATCCAGTAAAAATATGATAAGATTATTTCAGAATATGAAGAACTCTGTTTGTTTT

6360 TGATGAAAAACAAACAAAAAAAATCCACCTAACGGAATCTCAATTTAACTAACAGCGGC

6420 CAAACTGAGAAGTTAAATTTGAGAAGGGGAAAAGGCGGATTTATACTTGTATTTAACTAT

6480 CTCCATTTTAACATTTTATTAAACCCCATACAAGTGAAAATCCTCTTTTACACTGTTCCT

6540 TTAGGTGATCGCGGAGGGACATTATGAGTGAAGTAAACCTAAAAGGAAATACAGATGAAT

6600 TAGTGTATTATCGACAGCAAACCACTGGAAATAAAATCGCCAGGAAGAGAATCAAAAAAG

6660 GGAAAGAAGAAGTTTATTATGTTGCTGAAACGGAAGAGAAGATATGGACAGAAGAGCAAA

6720 TAAAAAACTTTTCTTTAGACAAATTTGGTACGCATATACCTTACATAGAAGGTCATTATA

6780 CAATCTTAAATAATTACTTCTTTGATTTTGGGGCTATTTTTTAGGTGCTGAAGGAATTG

6840 CGCTCTATGCTCACCTAACTCGTTATGCATACGGCAGCAAAGACTTTTGCTTTCCTAGTC

6900 TACAAACAATCGCTAAAAAAATGGACAAGACTCCTGTTACAGTTAGAGGCTACTTGAAAC

6960 TGCTTGAAAGGTACGGTTTTATTTGGAAGGTAAACGTCCGTAATAAAACCAAGGATAACA

7020 CAGAGGAATCCCCGATTTTTAAGATTAGACGTAAGGTTCCTTTGCTTTCAGAAGAACTTT

7080 TAAATGGAAACCCTAATATTGAAATTCCAGATGACGAGGAAGCACATGTAAAGAAGGCTT

7140 TAAAAAAGGAAAAAGAGGGTCTTCCAAAGGTTTTGAAAAAAGAGCACGATGAATTTGTTA
```

```
7200  AAAAAATGATGGATGAGTCAGAAACAATTAATATTCCAGAGGCCTTACAATATGACACAA
7260  TGTATGAAGATATACTCAGTAAAGGAGAAATTCGAAAAGAAATCAAAAAACAAATACCTA
7320  ATCCTACAACATCTTTTGAGAGTATATCAATGACAACTGAAGAGGAAAAAGTCGACAGTA
7380  CTTTAAAAAGCGAAATGCAAATCGTGTCTCTAAGCCTTCTTTTGATACCTGGTTTAAAA
7440  ACACTAAGATCAAAATTGAAAATAAAAATTGTTTATTACTTGTACCGAGTGAATTTGCAT
7500  TTGAATGGATTAAGAAAAGATATTTAGAAACAATTAAAACAGTCCTTGAAGAAGCTGGAT
7560  ATGTTTTCGAAAAAATCGAACTAAGAAAAGTGCAATAAACTGCTGAAGTATTTCAGCAGT
7620  TTTTTTTATTTAGAAATAGTGAAAAAAATATAATCAGGGAGGTATCAATATTTAATGAGT
7680  ACTGATTTAAATTTATTTAGACTGGAATTAATAATTAACACGTAGACTAATTAAAATTTA
7740  ATGAGGGATAAAGAGGATACAAAAATATTAATTTCAATCCCTATTAAATTTTAACAAGGG
7800  GGGGATTAAAATTTAATTAGAGGTTTATCCACAAGAAAAGACCCTAATAAAATTTTTACT
7860  AGGGTTATAACACTGATTAATTTCTTAATGGGGAGGGATTAAAATTTAATGACAAAGAA
                HindIII
7920  AACAATCTTTTAAGAAAAGCTTTTAAAAGATAATAATAAAAAGAGCTTTGCGATTAAGCA
7980  AAACTCTTTACTTTTTCATTGACATTATCAAATTCATCGATTTCAAATTGTTGTTGTATC
8040  ATAAAGTTAATTCTGTTTTGCACAACCTTTTCAGGAATATAAAACACATCTGAGGCTTGT
8100  TTTATAAACTCAGGGTCGCTAAAGTCAATGTAACGTAGCATATGATATGGTATAGCTTCC
8160  ACCCAAGTTAGCCTTTCTGCTTCTTCTGAATGTTTTTCATATACTTCCATGGGTATCTCT
8220  AAATGATTTTCCTCATGTAGCAAGGTATGAGCAAAAAGTTTATGGAATTGATAGTTCCTC
8280  TCTTTTTCTTCAACTTTTTTATCTAAAACAAACACTTTAACATCTGAGTCAATGTAAGCA
8340  TAAGATGTTTTTCCAGTCATAATTTCAATCCCAAATCTTTTAGACAGAAATTCTGGACGT
8400  AAATCTTTTGGTGAAAGAATTTTTTTATGTAGCAATATATCCGATACAGCACCTTCTAAA
8460  AGCGTTGGTGAATAGGGCATTTTACCTATCTCCTCTCATTTTGTGGAATAAAAATAGTCA
8520  TATTCGTCCATCTACCTATCCTATTATCGAACAGTTGAACTTTTTAATCAAGGATCAGTC
8580  CTTTTTTTCATTATTCTTAAACTGTGCTCTTAACTTTAACAACTCGATTTGTTTTCCAG
8640  ATCTCGAGGGTAACTAGCCTCGCCGATCCCGCAAGAGGCCCGGCAGTCAGGTGGCACTTT
8700  TCGGGGAAATGTGCGCGGAACCCCTATTTGTTTATTTTTCTAAATACATTCAAATATGTA
8760  TCCGCTCATGAGACAATAACCCTGATAAATGCTTCAATAATATTGAAAAAGGAAGAGTAT
8820  GAGTATTCAACATTTCCGTGTCGCCCTTATTCCCTTTTTTGCGGCATTTTGCCTTCCTGT
8880  TTTTGCTCACCCAGAAACGCTGGTGAAAGTAAAAGATGCTGAAGATCAGTTGGGTGCACG
8940  AGTGGGTTACATCGAACTGGATCTCAACAGCGGTAAGATCCTTGAGAGTTTTCGCCCCGA
9000  AGAACGTTTTCCAATGATGAGCACTTTTAAAGTTCTGCTATGTGGCGCGGTATTATCCCG
9060  TATTGACGCCGGGCAAGAGCAACTCGGTCGCCGCATACACTATTCTCAGAATGACTTGGT
9120  TGAGTACTCACCAGTCACAGAAAAGCATCTTACGGATGGCATGACAGTAAGAGAATTATG
9180  CAGTGCTGCCATAACCATGAGTGATAACACTGCGGCCAACTTACTTCTGACAACGATCGG
9240  AGGACCGAAGGAGCTAACCGCTTTTTTGCACAACATGGGGGATCATGTAACTCGCCTTGA
9300  TCGTTGGGAACCGGAGCTGAATGAAGCCATACCAAACGACGAGCGTGACACCACGATGCC
9360  TGTAGCAATGGCAACAACGTTGCGCAAACTATTAACTGGCGAACTACTTACTCTAGCTTC
9420  CCGGCAACAATTAATAGACTGGATGGAGGCGGATAAAGTTGCAGGACCACTTCTGCGCTC
9480  GGCCCTTCCGGCTGGCTGGTTTATTGCTGATAAATCTGGAGCCGGTGAGCGTGGGTCTCG
9540  CGGTATCATTGCAGCACTGGGGCCAGATGGTAAGCCCTCCCGTATCGTAGTTATCTACAC
```

```
-continued
 9600  GACGGGGAGTCAGGCAACTATGGATGAACGAAATAGACAGATCGCTGAGATAGGTGCCTC

9660  ACTGATTAAGCATTGGTAACTGTCAGACCAAGTTTACTCATATATACTTTAGATTGATTT

9720  AAAACTTCATTTTTAATTTAAAAGGATCTAGGTGAAGATCCTTTTTGATAATCTCATGAC

9780  CAAAATCCCTTAACGTGAGTTTTCGTTCCACTGAGCGTCAGACCCCGTAGAAAAGATCAA

9840  AGGATCTTCTTGAGATCCTTTTTTTCTGCGCGTAATCTGCTGCTTGCAAACAAAAAAACC

9900  ACCGCTACCAGCGGTGGTTTGTTTGCCGGATCAAGAGCTACCAACTCTTTTTCCGAAGGT

9960  AACTGGCTTCAGCAGAGCGCAGATACCAAATACTGTCCTTCTAGTGTAGCCGTAGTTAGG

10020  CCACCACTTCAAGAACTCTGTAGCACCGCCTACATACCTCGCTCTGCTAATCCTGTTACC

10080  AGTGGCTGCTGCCAGTGGCGATAAGTCGTGTCTTACCGGGTTGGACTCAAGACGATAGTT

10140  ACCGGATAAGGCGCAGCGGTCGGGCTGAACGGGGGGTTCGTGCACACAGCCCAGCTTGGA

10200  GCGAACGACCTACACCGAACTGAGATACCTACAGCGTGAGCTATGAGAAAGCGCCACGCT

10260  TCCCGAAGGGAGAAAGGCGGACAGGTATCCGGTAAGCGGCAGGGTCGGAACAGGAGAGCG

10320  CACGAGGGAGCTTCCAGGGGGAAACGCCTGGTATCTTTATAGTCCTGTCGGGTTTCGCCA

10380  CCTCTGACTTGAGCGTCGATTTTTGTGATGCTCGTCAGGGGGCGGAGCCTATGGAAAAA

10440  CGCCAGCAACGCGGCCTTTTTACGGTTCCTGGCCTTTTGCTGGCCTTTTGCTCACATGTT

10500  CTTTCCTGCGTTATCCCCTGATTCTGTGGATAACCGTATTACCGCCTTTGAGTGAGCTGA

10560  TACCGCTCGCCGCAGCCGAACGACCGAGCGCAGCGAGTCAGTGAGCGAGGAAGCGGAAGA

10620  GCGCCCAATACG
```

In this sequence the hasA gene is present between bases 2808 and 4062, and a Shine-Dalgarno sequence (GGAGGA) is correctly present before the gene to increase the efficiency of transcription. Next, the tuaD gene is present between bases 4105 bp to 5490 bp; here again, an efficient Shine-Dalgarno sequence (AGGAGA) is present before the gene. Moreover, the start codon of valine present in the tuaD gene was replaced with the more efficient methionine. The plasmid, tested for restriction enzymes HindIII and EcoRI, gives a correct restriction pattern with the following bands: 3957 bp, 1650 bp, 1522 bp, 1243 bp and 610 bp.

This vector is able to express hyaluronic acid in *Bacillus subtilis*, and also in *E. Coli*; in fact, the carbazole test, performed towards cells transacted with pBS5 with respect to cells containing the vector without these sequences shows the presence of glucuronic acid (FIG. 5—peak around 530 nm), which is one of the constituents of hyaluronic acid, exclusively in the cells engineered with pBS5.

Plasmid pHT01 is a shuttle vector able to grow in both *E. coli* and *B. subtilis*. However, it has been surprisingly found that the plasmid can be grown more efficiently in *E. Coli* cell strain INV-1α than in strain TOP-10, which is much more efficient in the transformation, because it contains the constitutively expressed lac repressor, Plasmid pBS5 contains the inducible promoter Pgrac which uses the lac repressor. Also in *E. coli*, this promoter, induced with 1 mM IPTG, allows the bacterial polymerases to code for the downstream genes for the HA synthesis. Then, the Applicant has obtained the transformation of this plasmid (to) in *E. coli* JM110 cells, bacterial cells lacking two genes. Dam and Dcm, which lead to DNA methylation at the level of recognition sequence GATC (Dam) and CCAGG CCTGG (Dcm). This DNA transferred to the *B. subtilis* cells is able to produce hyaluronic acid with a higher weight average molecular weight than that obtainable with DNA transferred in *E. coli* INV-1α strain.

Example 5

Bacterial Transformation in *Bacillus subtilis*

Media and Bacterial Strains for the Formation of Competent Cells

The transfer of engineered plasmids to *Bacillus subtilis* uses the natural entry capacity of the plasmids during a given step of bacterial growth, and is consequently a natural effect. The transformations with pBS5 were performed with different bacterial strains, in particular WB800N (MOBITEC) or 1.012 (MOBITEC). The first bacterial strain was developed for the expression of recombinant proteins because it lacks eight proteases which could degrade the proteins secreted in particular (the product of the hasA gene, hyaluronan synthase, is a transmembrane protein which could therefore undergo proteolysis). Strain 1012 was used as host cell for the expression of the plasmids of series pHT.

The following media axe required for the transformation:
Stock Solution of Metals 1000×
2 M $MgCl_2$
0.7 M $CaCl_2$
50 mM $MnCl_2$
5 mM $FeCl_3$
1 mM $ZnCl_2$
10× S-Base 10×MM
2 g $(NH_4)_2SO_4$
14 g $K_2HPO_4$
6 g $KH_2PO_4$
add distilled water to 100 ml and autoclave
HS Medium
For 100 ml:
10 ml 10×S-base
12.5 ml 4% glucose (m/v)
5 ml 0.1% L-tryptophan (m/v)

2 ml 1% casaminoacids (m/v)
25 ml 2% yeast extract (m/v)
10 ml 8% arginine (m/v), 0.4% histidine (m/v)
10 ml 1% sodium citrate (m/v)
0.01 ml 1M MgSO$_4$
25.49 ml distilled water
LS Medium
For 100 ml:
10 ml 10×S-base
12.5 ml 4% glucose (m/v)
0.5 ml 0.1% L-tryptophan (m/v)
1 ml 1% casaminoacids (m/v)
5 ml 2% yeast extract (m/v)
0.5 ml 0.5M MgCl$_2$
0.5 ml 0.1M CaCl$_2$
10 ml 1% sodium citrate (m/v)
0.01 ml 1M MgSO$_4$
59.990 ml distilled water Example 6

Preparation of Competent Cells from *Bacillus subtilis*

A single colony of *Bacillus subtilis* is grown overnight in 5 ml of HS medium at 37° C. The next day, 500 µl of this culture is incubated with 50 ml of HS medium and again grown under vigorous stirring at 200 rpm. When the cells have reached the steady state, 10 ml aliquots are collected every 15 minutes. 1 ml of glycerol is added to each aliquot, which is left on ice for 15 minutes. 1 ml aliquots are then taken and stored at −80° C. until use. The fractions with the highest rate of transformation are used for the following transformations.

Example 7

Transformation of Competent *Bacillus subtilis* Cells and Their Selection on IPTG Gradient The bacterial cells rendered competent are thawed rapidly in a thermostatic bath at 37° C., diluted in 20 ml of LS medium in a 250 ml Erlenmeyer flask, and placed under stirring for 2 hours at 30° C. When that time has elapsed, 1 ml aliquots are placed in 15 ml tubes to which 10 µl of EDTA is added, and maintained at ambient temperature for 5 minutes. Plasmid DNA pBS5 is added to the test tube and incubated for 2 h at 37° C., under stirring, with the maximum aeration. After gentle centrifugation the cells are plated in pre-heated selective medium. The bacterial colonies are obtained after two days. The cells cannot be grown in solution because they grow very slowly, and die after the addition of IPTG; above all, the few living cells no longer contain the recombinant plasmid. To select viable bacteria able to express high levels of hyaluronic acid, the cells were plated in the presence of an IPTG gradient. As shown in FIG. 6, the cells placed near a high concentration of IPTG die (because the tuaD expressed at high levels is toxic to *B. subtilis*); however, the cells plated in a position where a lower dose of IPTG occurs survived.

When the latter were examined, they presented as large, translucent colonies (FIG. 7), indicating the expression of hyaluronic acid; these cells, selected and grown in the presence of IPTG, also survive at higher doses of IPTG and preserve the plasmid during fermentation.

Through this system of selection viable bacterial lines are obtained, which are stable and above all secrete high levels of hyaluronic acid even after many cell divisions.

The stability of the plasmid was verified by growing the cells for 24 hours in the presence of IPTG and saccharose, and in the presence or absence of chloramphenicol. As clearly shown in FIG. 8, the number of colonies remains identical, demonstrating what has been stated, because plasmid contains chloramphenicol resistance gene, while the strain which has not been transfected, is devoid of said gene.

Example 8

Fermentation of Transformed, Selected *B. subtilis* Cells

*Bacillus subtilis* cells transformed with pBS5 plasmid and selected on IPTG gradient were cultured in a 20 L fermenter in 5 L of MM++ medium and glucose or saccharose as carbon source.

IPTG was added as inductor after the start of fermentation.

In the following, some fermentation processes for the production of HA having different weight average molecular weights are illustrated, said processes mainly differing because of:
the starting source of carbon;
the added feed (glucose or saccharose), activated about 7 hours after induction with IPTG 0.4-0.5 mM;
the occurred fermentation time and therefore the final cells mass obtained;
the temperature of fermentation (the temperature of fermentation can be established in a range between 20° C. and 38° C.).

Example 8a

Production of HA Having a Weight Average MW Comprised in the Range of 100-500 KD The bacterial strain *B. Subtilis* 1012, transfected with the plasmid pBS5 selected in IPTG gradient as described in Example 7, was used.

Procedure: a single colony resistant to IPTG was inoculated into 5 ml of sterile LB medium containing 10 µM of chloramphenicol, 10 µM of neomycin and 0.05 mM of IPTG. The culture was grown at 37° C., under stirring at 200 rpm.

After 8 hours, 50 µl of this culture were inoculated into a flask containing 50 ml of the medium mentioned above (with 0.5 mM of IPTG), and it was made to grow under the same conditions described above.

Subsequently, spent further 14-16 hours, 2 ml of this culture were inoculated into a flask containing 500 ml of the medium above, and it was made to grow under the same conditions until reaching a O.D.$^{600nm}$ of 0.6-0.8.

500 ml of the culture thus obtained were then inoculated in the fermenter and the fermentation conditions involved maintaining the culture under stirring at 1300 rpm, aeration with 10-12 liters of air/min, a temperature of 37° C. and a pH of 6.9 to 7.1. The initial source of carbon was 1% glucose.

After 6 hours of fermentation, a 2% glucose supply was added. At 24 hours of fermentation, IPTG was added to a final concentration of 0.4 mM; this induction proceeded for 6 hours; at the end, 10% glucose was added in stages.

At the end of fermentation (130 hours), the bacterial culture was discharged and centrifuged at 7500 rpm at 8° C. for 20 minutes.

The fermentation broth thus obtained, clarified as free of the cellular component, was analyzed to determine the concentration of HA with the carbazole method (Bitter and Muir, 1962, *Anal. Biochem.* 4:330-334).

Results: The analysis resulted in a concentration of HA of 7.5 g/l.

Determination of weight average molecular weight MW:

For its analysis it was used the method, of the intrinsic viscosity (as described in Terbojevich et al., *Carbohydr. Res,* 1986, 363-377, incorporated herein by reference).

Results: the analyzed HA sample showed a weight average molecular weight MW in the range of 200-400 KD.

Culture media used:

LB broth (Miller), pH 7

MM++ (Minimal Medium Bs), containing per liter:

5 g $NH_4Cl$; 1 g $NH_4NO_3$; 3 g $K_2HPO_4$; 1 g $KH_2PO_4$; 1 g $Na_2SO_4$ to the sterile media they were added 100 ml of a sterile solution containing:

0.1 g $MgSO_4.7H_2O$; 0.005 g $CaCl_2.2H_2O$; 2 ml biotine solution (biotine solution 1 mg/l); 1 ml Fe solution ($FeCl_3$ solution 0.2M); yeast extract 5 g/l, 0.01% Hydrolyzed Casein; uracil 5 mg/l, DL-tryptophan 5 mg/l; Histidine 400 µg/l; Arginine 400 µg/l; glucose solution (1% per liter).

Example 8b

Production of HA Having a Weight Average MW Comprised in the Range of 500-1000 KD The bacterial strain *B. Subtilis* WB800N, transfected with the plasmid pBS5 selected in IPTG gradient as described in Example 7, was used.

Procedure: a single colony resistant to IPTG was treated as above disclosed according to example 8a. The initial source of carbon was saccharose at 2%. The fermentation conditions involved maintaining the culture under stirring at 600 rpm, aeration with 22-24 liters of air/min, a temperature of 37° C. and a pH of 6.9 to 7.1.

After 6 hours of fermentation, IPTG was added to a final concentration of 0.4 mM; this induction proceeded for about 4 hours; at the end, 3% saccharose was added in stages, monitoring its concentration in the culture up to the end of fermentation (ended after 62 hours).

The culture media used for the fermentation were those disclosed according to example 8a.

At the end of the process, the fermentation broth was analyzed to determine the concentration of HA with the carbazole method.

Results; the analysis resulted in a concentration of HA of 4.0 g/l.

Determination of weight average molecular weight MW:

For its analysis it was used the method of the intrinsic viscosity as indicated in the previous example 8a.

Results: the analyzed HA sample showed a weight average molecular weight MW in the range of 550-800 KD.

Example 8c

Production of HA Having a Weight Average MW Comprised in the Range of $1\times10^6$-$2\times10^6$ D The bacterial strain *B. Subtilis* 1012, transfected with the plasmid pBS5 selected in IPTG gradient as described in Example 7, was used.

Procedure: a single colony resistant to IPTG was treated as above disclosed according to example 8a. The initial source of carbon was saccharose at 2%: in this example the further supply was glucose (further experimental, tests showed that it can be substituted with equal or lower amounts of saccharose). The fermentation conditions were the same as those used in example 8a, but the fermentation temperature was of 30° C.

The culture media used for the fermentation were those disclosed according to example 8a.

Cell mass development was of 30 g/l after 20 hours.

At the end of the process (ended after 35 hours), the fermentation broth was analyzed to determine the concentration of HA with the carbazole method.

Results: the analysis resulted in a concentration of HA of 3.3 g/l.

Determination of weight average molecular weight MW:

For its analysis it was used the method of the intrinsic viscosity as indicated in the previous example 8a.

Results: the analyzed HA sample showed a weight average molecular weight MW in the range of $1.5\times10^6$-$2\times10^6$D.

The system engineered in *B. subtilis* is inducible, so the fermentation process can be continued by stimulating the production of HA to obtain the desired weight average molecular weight MW; fermentation times between 80 and 160 hours result in a medium-low weight average molecular weight MW, comprised in the range between 100-500 KD, fermentation times between 40 and 80 hours result in a weight average molecular weight in the range between 500-1000 KD, fermentation times between 12 and 40 hours result in a weight average molecular weight MW in the range $1\times10^6$-$2\times10^6$ D. With the experiments and the results obtained above, the Applicant has demonstrated to have perfected a system of production of HA in *B. subtilis* by plasmid vectors by:

engineering of 2 genes (or 4 genes) plasmid vectors for the synthesis of enzymes needed for the production of said polysaccharide, whose gene control is placed under the control of inducible promoter Pgrac;

perfecting a system of selection of these transfected strains of *B. subtilis*, for the production of stable, viable, replicating and HA secreting strains;

creating an inducible system of HA production, thus controllable both in order to obtain high concentrations of HA and for the production of said polysaccharide at different weight average molecular weight MW.

The invention claimed is:

1. A method for obtaining recombinant bacterial host cells that produce hyaluronic acid, comprising selecting bacterial host cells on an IPTG gradient, wherein said bacterial host cells are from the genus *Escherichia* or *Bacillus* and comprise at least one plasmid vector comprising a strong inducible promoter Pgrac operationally linked to a nucleic acid encoding a hyaluronan synthase enzyme and a nucleic acid encoding a UDP-glucose dehydrogenase enzyme in tandem, said plasmid vector comprising the nucleotide sequence of SEQ ID NO: 1.

2. The method according to claim 1, wherein said plasmid vector comprises a nucleotide sequence coding for a UDP-glucose pyrophosphorylase enzyme and a nucleotide sequence coding for a glucose 6 phosphate isomerase enzyme.

3. The method according to claim 1, wherein said plasmid vector comprises a nucleotide sequence coding for a lac repressor.

4. The method according to claim 1, wherein said hyaluronan synthase is encoded by a hasA gene from *Streptococcus zooepidemicus*, and said UDP-glucose dehydrogenase is encoded by a tuaD gene from *Bacillus subtilis*.

5. The method according to claim 2, wherein the nucleotide sequences coding for the enzymes hyaluronan synthase, UDP-glucose dehydrogenase, UDP-glucose pyrophosphorylase and glucose 6 phosphate isomerase are operatively linked to an upstream Shine-Dalgarno sequence.

6. The method according to claim 1, wherein said bacterial host cells are *Bacillus subtilis* WB800N cells or *Bacillus subtilis* 1012 cells.

7. The method according to claim 1, wherein said bacterial host cells are *Escherichia coli* BL21 cells.

8. The method according to claim 2, wherein the nucleic acid encoding the hyaluronan synthase (hasA) is obtained from a strain of *Streptococcus*, and the nucleic acids encoding the UDP-glucose dehydrogenase (hasB or tuaD), UDP-glucose pyrophosphorylase (hasC or gtaB) and glucose 6 phosphate isomerase (hasE or pgi) are derived from *Bacillus subtilis*.

* * * * *

SEQUENCE LISTING

```
<160> NUMBER OF SEQ ID NOS: 12

<210> SEQ ID NO 1
<211> LENGTH: 10632
<212> TYPE: DNA
<213> ORGANISM: Artificial Sequence
<220> FEATURE:
<223> OTHER INFORMATION: Plasmid containing hasA and tuaD gene under the
      control of promoter grac

<400> SEQUENCE: 1
```

-continued

```
ttaagttatt ggtatgactg gttttaagcg caaaaaaagt tgcttttcg tacctattaa      60 tgtatcgttt tagaaaaccg actgtaaaaa gtacagtcgg cattatctca tattataaaa    120
gccagtcatt aggcctatct gacaattcct gaatagagtt cataaacaat cctgcatgat    180
aaccatcaca aacagaatga tgtacctgta aagatagcgg taaatatatt gaattacctt    240
tattaatgaa ttttcctgct gtaataatgg gtagaaggta attactatta ttattgatat    300
ttaagttaaa cccagtaaat gaagtccatg gaataataga aagagaaaaa gcattttcag    360
gtataggtgt tttgggaaac aatttccccg aaccattata tttctctaca tcagaaaggt    420
ataaatcata aaactctttg aagtcattct ttacaggagt ccaaatacca gagaatgttt    480
tagatacacc atcaaaaatt gtataaagtg gctctaactt atcccaataa cctaactctc    540
cgtcgctatt gtaaccagtt ctaaaagctg tatttgagtt tatcacccct gtcactaaga    600
aaataaatgc agggtaaaat ttatatcctt cttgttttat gtttcggtat aaaacactaa    660
tatcaatttc tgtggttata ctaaaagtcg tttgttggtt caaataatga ttaaatatct    720
cttttctctt ccaattgtct aaatcaattt tattaaagtt catttgatat gcctcctaaa    780
tttttatcta aagtgaattt aggaggctta cttgtctgct ttcttcatta gaatcaatcc    840 tttttttaaaa gtcaatatta ctgtaacata aatatatatt ttaaaaatat cccactttat    900
ccaattttcg tttgttgaac taatgggtgc tttagttgaa gaataaagac cacattaaaa    960
aatgtggtct tttgtgtttt tttaaaggat ttgagcgtag cgaaaaatcc tttctttct   1020 tatcttgata ataagggtaa ctattgccga tcgtccattc cgacagcatc gccagtcact   1080
atggcgtgct gctagcgcca ttcgccattc aggctgcgca actgttggga agggcgatcg   1140
gtgcgggcct cttcgctatt acgccagctg gcgaaagggg gatgtgctgc aaggcgatta   1200
agttgggtaa cgccagggtt ttcccagtca cgacgttgta aaacgacggc cagtgaattc   1260
gagctcaggc cttaactcac attaattgcg ttgcgctcac tgcccgcttt ccagtcggga   1320
aacctgtcgt gccagctgca ttaatgaatc ggccaacgcg cggggagagg cggtttgcgt   1380
attgggcgcc agggtggttt ttcttttcac cagtgagacg ggcaacagct gattgccctt   1440
caccgcctgg ccctgagaga gttgcagcaa gcggtccacg ctggtttgcc ccagcaggcg   1500
aaaatcctgt ttgatggtgg ttgacggcgg gatataacat gagctgtctt cggtatcgtc   1560
gtatcccact accgagatat ccgcaccaac gcgcagcccg gactcggtaa tggcgcgcat   1620
tgcgcccagc gccatctgat cgttggcaac cagcatcgca gtgggaacga tgccctcatt   1680
cagcatttgc atggtttgtt gaaaccgga catggcactc cagtcgcctt cccgttccgc   1740
tatcggctga atttgattgc gagtgagata tttatgccag ccagccagac gcagacgcgc   1800
cgagacagaa cttaatgggc ccgctaacag cgcgatttgc tggtgaccca atgcgaccag   1860
atgctccacg cccagtcgcg taccgtcttc atgggagaaa ataatactgt tgatgggtgt   1920
ctggtcagag acatcaagaa ataacgccgg aacattagtg caggcagctt ccacagcaat   1980
ggcatcctgg tcatccagcg gatagttaat gatcagccca ctgacgcgtt gcgcgagaag   2040
attgtgcacc gccgctttac aggcttcgac gccgcttcgt tctaccatcg acaccaccac   2100
gctggcaccc agttgatcgg cgcgagattt aatcgccgcg acaatttgcg acggcgcgtg   2160
cagggccaga ctggaggtgg caacgccaat cagcaacgac tgtttgcccg ccagttgttg   2220
tgccacgcgg ttgggaatgt aattcagctc cgccatcgcc gcttccactt tttcccgcgt   2280
tttcgcagaa acgtggctgg cctggttcac cacgcgggaa acggtctgat aagagacacc   2340
```

```
ggcatactct gcgacatcgt ataacgttac tggtttcatc aaaatcgtct ccctccgttt    2400
gaatatttga ttgatcgtaa ccagatgaag cactcttttcc actatcccta cagtgttatg   2460
gcttgaacaa tcacgaaaca ataattggta cgtacgatct ttcagccgac tcaaacatca    2520
aatcttacaa atgtagtctt tgaaagtatt acatatgtaa gatttaaatg caaccgtttt    2580
ttcggaagga aatgatgacc tcgtttccac cggaattagc ttggtaccag ctattgtaac    2640
ataatcggta cggggtgaa aaagctaacg gaaaagggag cggaaaagaa tgatgtaagc     2700
gtgaaaaatt ttttatctta tcacttgaaa ttggaaggga gattctttat tataagaatt   2760
gtggaattgt gagcggataa caattcccaa ttaaaggagg aaggatccat gagaacatta    2820
aaaaacctca taactgttgt ggcctttagt atttttggg tactgttgat ttacgtcaat     2880
gtttatctct ttggtgctaa aggaagcttg tcaatttatg gcttttttgct gatagcttac   2940 ctattagtca aaatgtcctt atccttttttt tacaagccat ttaagggaag ggctgggcaa   3000
tataaggttg cagccattat tccctcttat aacgaagatg ctgagtcatt gctagagacc    3060
ttaaaaagtg ttcagcagca aacctatccc ctagcagaaa tttatgttgt tgacgatgga    3120
agtgctgatg agacaggtat taagcgcatt gaagactatg tgcgtgacac tggtgaccta    3180
tcaagcaatg tcattgttca ccggtcagaa aaaatcaag gaaagcgtca tgcacaggcc     3240
tgggcctttg aaagatcaga cgctgatgtc tttttgaccg ttgactcaga tacttatatc    3300
taccctgatg ctttagagga gttgttaaaa acctttaatg acccaactgt ttttgctgcg    3360
acgggtcacc ttaatgtcag aaatagacaa accaatctct taacacgctt gacagatatt    3420
cgctatgata atgcttttgg cgttgaacga gctgcccaat ccgttacagg taatattctc    3480
gtttgctcag gcccgcttag cgtttacaga cgcgaggtgg ttgttcctaa catagataga    3540
tacatcaacc agaccttcct gggtattcct gtaagtatcg gtgatgacag gtgcttgacc    3600
aactatgcaa ctgatttagg aaagactgtt tatcaatcca ctgctaaatg tattacagat    3660
gttcctgaca agatgtctac ttacttgaag cagcaaaacc gctggaacaa gtccttctt    3720 agagagtcca ttatttctgt taagaaaatc atgaacaatc cttttgtagc cctatggacc    3780
atacttgagg tgtctatgtt tatgatgctt gtttattctg tggtggattt ctttgtaggc    3840
aatgtcagag aatttgattg gctcagggtt ttggccttc tggtgattat cttcattgtt    3900
gctctttgtc gtaatattca ctatatgctt aagcacccgc tgtccttctt gttatctccg    3960
ttttatgggg tactgcattt gtttgtccta cagcccttga aattgtattc tcttttttact   4020 attagaaatg ctgactgggg aacacgtaaa aaattattat aatctagaaa taattttgtt    4080
taactttaag aaggagatat acatatgaaa aaaatagctg tcattggaac aggttatgta    4140
ggactcgtat caggcacttg ctttgcggag atcggcaata aagttgtttg ctgtgatatc    4200
gatgaatcaa aaatcagaag cctgaaaaat ggggtaatcc caatctatga accagggctt    4260
gcagacttag ttgaaaaaaa tgtgctggat cagcgcctga cctttacgaa cgatatcccg    4320
tctgccattc gggcctcaga tattatttat attgcagtcg gaacgcctat gtccaaaaca    4380
ggtgaagctg atttaacgta cgtcaaagcg gcggcgaaaa caatcggtga gcatcttaac    4440
ggctacaaag tgatcgtaaa taaagcaca gtcccggttg gaacagggaa actggtgcaa    4500
tctatcgttc aaaaagcctc aagggggaga tactcatttg atgttgtatc taaccctgaa    4560
ttccttcggg aagggtcagc gattcatgac acgatgaata tggagcgtgc cgtgattggt    4620
tcaacaagtc ataagccgc tgccatcatt gaggaacttc atcagccatt ccatgctcct    4680
gtcattaaaa caaacctaga aagtgcagaa atgattaaat acgccgcgaa tgcatttctg    4740
```

```
gcgacaaaga tttcctttat caacgatatc gcaaacattt gtgagcgagt cggcgcagac    4800
gtttcaaaag ttgctgatgg tgttggtctt gacagccgta tcggcagaaa gttccttaaa    4860
gctggtattg gattcggcgg ttcatgtttt ccaaaggata caaccgcgct gcttcaaatc    4920
gcaaaatcgg caggctatcc attcaagctc atcgaagctg tcattgaaac gaacgaaaag    4980
cagcgtgttc atattgtaga taaacttttg actgttatgg gaagcgtcaa agggagaacc    5040
atttcagtcc tgggattagc cttcaaaccg aatacgaacg atgtgagatc cgctccagcg    5100
cttgatatta tcccaatgct gcagcagctg ggcgcccatg taaaagcata cgatccgatt    5160
gctattcctg aagcttcagc gatccttggc gaacaggtcg agtattacac agatgtgtat    5220
gctgcgatgg aagacactga tgcatgcctg attttaacgg attggccgga agtgaaagaa    5280
atggagcttg taaagtgaaa accctcttaa aacagccag tcatcattga cggcagaaat      5340 ttatttttcac ttgaagagat gcaggcagcc ggatacattt atcactctat cggccgtccc    5400
gctgttcggg gaacggaacc ctctgacaag tattttccgg gcttgccgct gaagaattg      5460 gctaaagact tgggaagcgt caatttataa gctagagtcg acgtccccgg ggcagcccgc     5520
ctaatgagcg ggcttttttc acgtcacgcg tccatggaga tctttgtctg caactgaaaa     5580
gtttatacct tacctggaac aaatggttga acatacgag gctaatatcg gcttattagg      5640
aatagtccct gtactaataa atcaggtgg atcagttgat cagtatattt tggacgaagc      5700
tcggaaagaa tttggagatg acttgcttaa ttccacaatt aaattaaggg aaagaataaa     5760
gcgatttgat gttcaaggaa tcacggaaga agatactcat gataaagaag ctctaaaact     5820
attcaataac cttacaatgg aattgatcga aagggtggaa ggttaatggt acgaaaatta     5880
ggggatctac ctagaaagcc acaaggcgat aggtcaagct taagaaccc ttacatggat      5940 cttacagatt ctgaaagtaa agaaacaaca gaggttaaac aaacagaacc aaaaagaaaa     6000
aaagcattgt tgaaaacaat gaaagttgat gtttcaatcc ataataagat taaatcgctg     6060
cacgaaattc tggcagcatc cgaagggaat tcatattact tagaggatac tattgagaga     6120
gctattgata gatggttga gacattacct gagagccaaa aaacttttta tgaatatgaa      6180
ttaaaaaaaa gaaccaacaa aggctgagac agactccaaa cgagtctgtt tttttaaaaa     6240
aaatattagg agcattgaat atatattaga gaattaagaa agacatggga ataaaaatat     6300
tttaaatcca gtaaaaatat gataagatta tttcagaata tgaagaactc tgtttgtttt    6360
tgatgaaaaa acaaacaaaa aaaatccacc taacggaatc tcaatttaac taacagcggc    6420
caaactgaga agttaaattt gagaagggga aaaggcggat ttatacttgt atttaactat    6480
ctccatttta acattttatt aaacccata caagtgaaaa tcctcttta cactgttcct      6540 ttaggtgatc gcggagggac attatgagtg aagtaaacct aaaaggaaat acagatgaat    6600
tagtgtatta tcgacagcaa accactggaa ataaaatcgc caggaagaga atcaaaaaag    6660
ggaaagaaga agtttattat gttgctgaaa cggaagagaa gatatggaca gaagagcaaa    6720
taaaaaactt ttctttagac aaatttggta cgcatatacc ttacatagaa ggtcattata    6780
caatcttaaa taattacttc tttgattttt ggggctattt tttaggtgct gaaggaattg    6840
cgctctatgc tcacctaact cgttatgcat acggcagcaa agacttttgc tttcctagtc    6900
tacaaacaat cgctaaaaaa atggacaaga ctcctgttac agttagaggc tacttgaaac    6960
tgcttgaaag gtacggtttt atttggaagg taaacgtccg taataaaacc aaggataaca    7020
cagaggaatc cccgattttt aagattagac gtaaggttcc tttgctttca gaagaacttt    7080
```

-continued

```
taaatggaaa ccctaatatt gaaattccag atgacgagga agcacatgta aagaaggctt    7140
taaaaaagga aaaagagggt cttccaaagg ttttgaaaaa agagcacgat gaatttgtta    7200
aaaaaatgat ggatgagtca gaaacaatta atattccaga ggccttacaa tatgacacaa    7260
tgtatgaaga tatactcagt aaaggagaaa ttcgaaaaga aatcaaaaaa caaatacctca   7320
atcctacaac atcttttgag agtatatcaa tgacaactga agaggaaaaa gtcgacagta    7380
ctttaaaaag cgaaatgcaa aatcgtgtct ctaagccttc ttttgatacc tggtttaaaa    7440
acactaagat caaaattgaa aataaaaatt gtttattact tgtaccgagt gaatttgcat    7500
ttgaatggat taagaaaaga tatttagaaa caattaaaac agtccttgaa gaagctggat    7560
atgttttcga aaaaatcgaa ctaagaaaag tgcaataaac tgctgaagta tttcagcagt    7620
tttttttatt tagaaatagt gaaaaaaata taatcaggga ggtatcaata tttaatgagt    7680
actgatttaa atttatttag actggaatta ataattaaca cgtagactaa ttaaaattta    7740
atgagggata aagaggatac aaaaatatta atttcaatcc ctattaaatt ttaacaaggg    7800
ggggattaaa atttaattag aggtttatcc acaagaaaag accctaataa aattttttact   7860
agggttataa cactgattaa tttcttaatg ggggagggat taaaatttaa tgacaaagaa    7920
aacaatcttt taagaaaagc ttttaaaaga taataataaa aagagctttg cgattaagca    7980
aaactcttta cttttttcatt gacattatca aattcatcga tttcaaattg ttgttgtatc    8040
ataaagttaa ttctgtttg cacaaccttt tcaggaatat aaaacacatc tgaggcttgt     8100
tttataaact cagggtcgct aaagtcaatg taacgtagca tatgatatgg tatagcttcc    8160
acccaagtta gccttttctgc ttcttctgaa tgttttccat atacttccat gggtatctct   8220
aaatgatttt cctcatgtag caaggtatga gcaaaaagtt tatggaattg atagttcctc    8280
tctttttctt caactttttt atctaaaaca aacactttaa catctgagtc aatgtaagca    8340
taagatgttt ttccagtcat aatttcaatc ccaaatcttt tagacagaaa ttctggacgt    8400
aaatcttttg gtgaaagaat tttttttatgt agcaatatat ccgatacagc accttctaaa   8460
agcgttggtg aatagggcat tttacctatc tcctctcatt ttgtggaata aaaatagtca    8520
tattcgtcca tctacctatc ctattatcga acagttgaac ttttttaatca aggatcagtc   8580
ctttttttca ttattcttaa actgtgctct taactttaac aactcgattt gttttttccag   8640
atctcgaggg taactagcct cgccgatccc gcaagaggcc cggcagtcag gtggcacttt    8700
tcggggaaat gtgcgcggaa cccctatttg tttatttttc taaatacatt caaatatgta    8760
tccgctcatg agacaataac cctgataaat gcttcaataa tattgaaaaa ggaagagtat    8820
gagtattcaa catttccgtg tcgcccttat tccctttttt gcggcatttt gccttcctgt    8880
ttttgctcac ccagaaacgc tggtgaaagt aaaagatgct gaagatcagt tgggtgcacg    8940
agtgggttac atcgaactgg atctcaacag cggtaagatc cttgagagtt ttcgccccga    9000
agaacgtttt ccaatgatga gcactttttaa agttctgcta tgtggcgcgg tattatcccg    9060
tattgacgcc gggcaagagc aactcggtcg ccgcatacac tattctcaga atgacttggt    9120
tgagtactca ccagtcacag aaaagcatct tacggatggc atgacagtaa gagaattatg    9180
cagtgctgcc ataaccatga gtgataacac tgcggccaac ttacttctga caacgatcgg    9240
aggaccgaag gagctaaccg cttttttgca acatggggg atcatgtaa ctcgccttga    9300
tcgttgggaa ccggagctga atgaagccat accaaacgac gagcgtgaca ccacgatgcc    9360
tgtagcaatg gcaacaacgt tgcgcaaact attaactggc gaactactta ctctagcttc    9420
ccggcaacaa ttaatagact ggatggaggc ggataaagtt gcaggaccac ttctgcgctc    9480
```

```
ggcccttccg gctggctggt ttattgctga taaatctgga gccggtgagc gtgggtctcg      9540
cggtatcatt gcagcactgg ggccagatgg taagccctcc cgtatcgtag ttatctacac      9600
gacggggagt caggcaacta tggatgaacg aaatagacag atcgctgaga taggtgcctc      9660
actgattaag cattggtaac tgtcagacca agtttactca tatatacttt agattgattt      9720
aaaacttcat ttttaattta aaaggatcta ggtgaagatc cttttttgata atctcatgac     9780 caaaatccct taacgtgagt tttcgttcca ctgagcgtca gacccgtag aaaagatcaa       9840 aggatcttct tgagatcctt ttttttctgcg cgtaatctgc tgcttgcaaa caaaaaaacc    9900
accgctacca gcggtggttt gtttgccgga tcaagagcta ccaactcttt ttccgaaggt      9960
aactggcttc agcagagcgc agataccaaa tactgtcctt ctagtgtagc cgtagttagg    10020
ccaccacttc aagaactctg tagcaccgcc tacatacctc gctctgctaa tcctgttacc    10080
agtggctgct gccagtggcg ataagtcgtg tcttaccggg ttggactcaa gacgatagtt    10140
accggataag gcgcagcggt cgggctgaac ggggggttcg tgcacacagc ccagcttgga    10200
gcgaacgacc tacaccgaac tgagatacct acagcgtgag ctatgagaaa gcgccacgct    10260
tcccgaaggg agaaaggcgg acaggtatcc ggtaagcggc agggtcggaa caggagagcg    10320
cacgagggag cttccagggg gaaacgcctg gtatctttat agtcctgtcg ggtttcgcca    10380
cctctgactt gagcgtcgat ttttgtgatg ctcgtcaggg gggcggagcc tatgaaaaaa    10440
cgccagcaac gcggccttt tacggttcct ggccttttgc tggccttttg ctcacatgtt    10500
ctttcctgcg ttatccctg attctgtgga taaccgtatt accgcctttg agtgagctga    10560
taccgctcgc cgcagccgaa cgaccgagcg cagcgagtca gtgagcgagg aagcggaaga    10620
gcgcccaata cg                                                         10632

<210> SEQ ID NO 2
<211> LENGTH: 27
<212> TYPE: DNA
<213> ORGANISM: Artificial Sequence
<220> FEATURE:
<223> OTHER INFORMATION: tuaD gene amplification primer

<400> SEQUENCE: 2
atgaaaaaat agctgtcatt ggaacag                                          27

<210> SEQ ID NO 3
<211> LENGTH: 24
<212> TYPE: DNA
<213> ORGANISM: Artificial Sequence
<220> FEATURE:
<223> OTHER INFORMATION: tuaD gene amplification primer

<400> SEQUENCE: 3
ttataaattg tcgttcccaa gtct                                             24

<210> SEQ ID NO 4
<211> LENGTH: 31
<212> TYPE: DNA
<213> ORGANISM: Artificial Sequence
<220> FEATURE:
<223> OTHER INFORMATION: tuaD gene cloning primer

<400> SEQUENCE: 4
gctggatcca tgaaaaaata gctgtcattg g                                     31

<210> SEQ ID NO 5
```

```
<211> LENGTH: 31
<212> TYPE: DNA
<213> ORGANISM: Artificial Sequence
<220> FEATURE:
<223> OTHER INFORMATION: tuaD gene cloning primer

<400> SEQUENCE: 5
ctcgctagct tataaattga cgcttcccaa g                               31

<210> SEQ ID NO 6
<211> LENGTH: 28
<212> TYPE: DNA
<213> ORGANISM: Artificial Sequence
<220> FEATURE:
<223> OTHER INFORMATION: Amplification primer for the introduction of a
      Shine-Dalgarno sequence in the tuaDgene

<400> SEQUENCE: 6
cgacatatga aaaatagct gtcattgg                                    28

<210> SEQ ID NO 7
<211> LENGTH: 31
<212> TYPE: DNA
<213> ORGANISM: Artificial Sequence
<220> FEATURE:
<223> OTHER INFORMATION: Amplification primer for the introduction of a
      Shine-Dalgarno sequence in the tuaDgene

<400> SEQUENCE: 7
ctcgctagct tataaattga cgcttcccaa g                               31

<210> SEQ ID NO 8
<211> LENGTH: 26
<212> TYPE: DNA
<213> ORGANISM: Artificial Sequence
<220> FEATURE:
<223> OTHER INFORMATION: hasA gene amplification primer

<400> SEQUENCE: 8
atgagaacat taaaaaacct cataac                                     26

<210> SEQ ID NO 9
<211> LENGTH: 25
<212> TYPE: DNA
<213> ORGANISM: Artificial Sequence
<220> FEATURE:
<223> OTHER INFORMATION: hasA gene amplification primer

<400> SEQUENCE: 9
taataatttt ttacgtgttc cccag                                      25

<210> SEQ ID NO 10
<211> LENGTH: 32
<212> TYPE: DNA
<213> ORGANISM: Artificial Sequence
<220> FEATURE:
<223> OTHER INFORMATION: hasA gene cloning primer

<400> SEQUENCE: 10
ggaggatcca tgagaacatt aaaaaacctc at                              32

<210> SEQ ID NO 11
<211> LENGTH: 31
<212> TYPE: DNA
<213> ORGANISM: Artificial Sequence
<220> FEATURE:
<223> OTHER INFORMATION: hasA gene cloning primer
```

-continued

```
<400> SEQUENCE: 11
cagtctagat tataataatt tttacgtgtc c                              31

<210> SEQ ID NO 12
<211> LENGTH: 153
<212> TYPE: DNA
<213> ORGANISM: Artificial Sequence
<220> FEATURE:
<223> OTHER INFORMATION: Synthetic oligonucleotide

<400> SEQUENCE: 12
gaaaagaatg atgtaagcgt gaaaaatttt ttatcttatc acttgaaatt ggaagggaga      60
ttctttatta taagaattgt ggaattgtga gcggataaca attcccaatt aaaggaggaa     120
ggatcctcta gagtcgacgt ccccggggca gcc                                  153
```